United States Patent [19]

Müller-Gliemann et al.

[11] Patent Number: 5,356,911

[45] Date of Patent: Oct. 18, 1994

[54] SUBSTITUTED BIPHENYLPYRIDONES

[75] Inventors: Matthias Müller-Gliemann, Wuppertal; Martin Beuck, Erkrath; Stanislav Kazda; Johannes-Peter Stasch, both of Wuppertal; Andreas Knorr, Erkrath; Stefan Wohlfeil, Hilden; Walter Hübsch, Wuppertal; Jürgen Dressel, Wuppertal; Peter Fey, Wuppertal; Rudolf Hanko, Duesseldorf; Thomas Krämer, Wuppertal; Ulrich Müller, Wuppertal; Siegfried Zaiss, Wuppertal, all of Fed. Rep. of Germany

[73] Assignee: Bayer Aktiengesellschaft, Leverkusen, Fed. Rep. of Germany

[21] Appl. No.: 970,364

[22] Filed: Nov. 2, 1992

[30] Foreign Application Priority Data

Nov. 12, 1991 [DE] Fed. Rep. of Germany ....... 4137151
Jul. 1, 1992 [DE] Fed. Rep. of Germany ....... 4221583

[51] Int. Cl.$^5$ .................. C07D 401/10; A61K 31/44
[52] U.S. Cl. ................................... 514/340; 546/276
[58] Field of Search ..................... 546/276; 514/340

[56] References Cited

U.S. PATENT DOCUMENTS 5,100,897 3/1992 Allen et al. .................... 514/269

FOREIGN PATENT DOCUMENTS 2051705 12/1991 Canada .
0435827 7/1991 European Pat. Off. .
0445811 9/1991 European Pat. Off. .
0487745 6/1992 European Pat. Off. .
500297 8/1992 European Pat. Off. .
0500297 8/1992 European Pat. Off. .
0530702 3/1993 European Pat. Off. .
92/14714 9/1992 PCT Int'l Appl. .

OTHER PUBLICATIONS

Wade Jr. Organic Chemistry Princeton-Hall Inc. 1987, p. 349.
Angiotensin and cell growth: a link to cardiovascular hypertrophy?, Pierre Schelling, et al., Journal of Hypertension 1991.
J. C. Sheehan, S. L. Ledis, J. Am. Chem. Soc. 95, 875 (1973).
F. E. Frerman et al, J. Biol. Chem., 258, pp. 7087-7093 (1983).
N. B. Benoton, K. Kluroda, Int. Pept. Prot. Res. 17, 197 (1981).
Chemical Abstract, vol. 104, (1986), 224893.
Chemical Abstract, vol. 114, (1991), 247304.
Chemical Abstract, vol. 115, (1991), 114531.
Chemical Abstract, vol. 115, (1991), 159173.
J. Am. Chem. Soc., 73, (1951), 1368, R. P. Mariella, R. Stansfield.
O. Isler et al, Helv. Chim. Acta 38, 1033 (1955).
R. Ross, J. Cell. Biol. 50, pp. 172-186, (1971).

*Primary Examiner*—Jane T. Fan
*Attorney, Agent, or Firm*—Sprung Horn Kramer & Woods

[57] ABSTRACT

Substituted biphenylpyridones can be prepared by alkylating pyridones on the nitrogen. The substituted biphenylpyridones are suitable as active substances in medicaments, in particular in hypotensive and anti-atherosclerotic medicaments.

4 Claims, No Drawings

SUBSTITUTED BIPHENYLPYRIDONES

The invention relates to substituted biphenylpyridones, to processes for their preparation and to their use in medicaments, in particular as hypotensive and antiatherosclerotic agents.

It is known that renin, a proteolytic enzyme, eliminates the decapeptide angiotensin I from angiotensinogen in vivo, which decapeptide is in turn degraded in the lungs, the kidneys or other tissues to the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, of cardiac muscle cells and smooth muscle cells, where these grow in an increased manner in various disease states (for example hypertension, atherosclerosis and cardiac insufficiency) and proliferate.

In addition to the inhibition of renin activity, a possible starting point for intervention in the reninangiotensin system (RAS) is the inhibition of the activity of the angiotensin-converting enzyme (ACE) and the blockade of angiotensin II receptors.

Additionally, biphenyl-substituted pyrimidones have been disclosed in the publications EP 407,342, 424,317, 435,827 and 419,048.

The invention relates to substituted biphenylpyridones of the general formula (I)

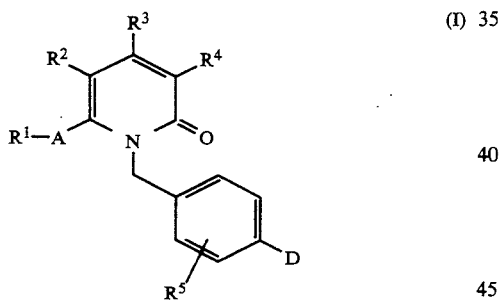

in which
$R^1$ represents straight-chain or branched alkyl having up to 10 carbon atoms, which is optionally substituted by cycloalkyl having 3 to 6 carbon atoms, hydroxyl or by straight-chain or branched alkoxy having up to 6 carbon atoms, or represents cycloalkyl having 3 to 6 carbon atoms or halogen, A represents a direct bond, or represents an oxygen or sulphur atom or represents the $-CH_2-$ group or the group of the formula $-NR^6$
in which
$R^6$ denotes hydrogen or straight-chain or branched alkyl having up to 6 carbon atoms, or
$R^6$, together with $R^1$ including the nitrogen atom, forms a 5- or 6-membered, saturated or unsaturated heterocycle, $R^2$, $R^3$ and $R^4$ are identical or different and represent hydrogen, nitro, cyano, formyl or halogen, or represent straight-chain or branched alkyl, alkenyl, alkinyl, alkoxy or alkylthio each having up to 8 carbon atoms, each of which is optionally substituted up to 2 times by identical or different substituents from the group comprising hydroxyl, cyano, halogen, carboxyl, straight-chain or branched alkoxy, acyl or alkoxycarbonyl each having up to 6 carbon atoms, or by benzyl, phenyl, phenoxy or benzoyl or by a 5- to 7-membered, saturated or unsaturated heterocycle having up to 3 heteroatoms, where the cycles can in turn be substituted up to 2 times by identical or different substituents from the group comprising trifluoromethyl, trifluoromethoxy, halogen, nitro, cyano, hydroxyl, hydroxymethyl or by straight-chain or branched alkyl or alkoxy each having up to 6 carbon atoms, or represent straight-chain or branched acyl or alkoxycarbonyl each having up to 8 carbon atoms, phenoxycarbonyl, benzyloxycarbonyl or carboxyl, or represent cycloalkyl or -alkenyl having 3 to 8 carbon atoms, or a 5- to 7-membered, unsaturated heterocycle having up to 3 heteroatoms from the series comprising S, N or O, phenyl, phenoxy and phenylthio, each of which is optionally substituted up to 3 times by identical or different substituents from the group comprising halogen, nitro, cyano, hydroxyl, hydroxymethyl, trifluoromethyl and trifluoromethoxy or by straight-chain or branched alkyl or alkoxy each having up to 6 carbon atoms, or, represent tetrazolyl which is optionally substituted by methyl or a trityl group or represent a group of the formula

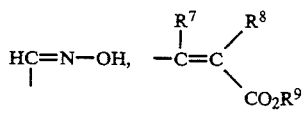

$-NR^{10}R^{11}$, $-CO-NR^{10}R^{11}$ or $-CH_2-OR^{12}$
in which
$R^7$ denotes hydrogen or straight-chain or branched alkyl having up to 6 carbon atoms,
$R^8$ denotes hydrogen or straight-chain or branched alkyl having up to 8 carbon atoms, which is optionally substituted by cycloalkyl having 3 to 6 carbon atoms, phenyl or by a 5- to 7-membered saturated or unsaturated heterocycle having up to 3 heteroatoms from the series comprising S, N and O, where the cycles are optionally substituted by hydroxyl, hydroxymethyl or halogen or by straight-chain or branched alkyl or alkoxy each having up to 6 carbon atoms, or denotes cycloalkyl having 3 to 6 carbon atoms or phenyl,
$R^9$ denotes hydrogen, straight-chain or branched alkyl having up to 8 carbon atoms or phenyl,
$R^{10}$ and $R^{11}$ are identical or different and denote hydrogen, cycloalkyl having 3 to 8 carbon atoms or straight-chain or branched alkyl having up to 8 carbon atoms, which is optionally substituted by phenyl,
$R^{12}$ denotes straight-chain or branched acyl having up to 6 carbon atoms or benzoyl, or
$-A-R^1$ and $R^2$ together represent an alkylene chain having up to 5 carbon atoms,
$R^5$ represents hydrogen, halogen, cyano, nitro, trifluoromethyl, hydroxyl, trifluoromethoxy or straight-chain or branched alkyl or alkoxy each having up to 6 carbon atoms,
D represents a radical of the formula

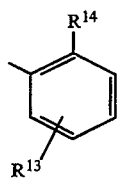

in which $R^{13}$ has the abovementioned meaning of $R^5$ and is identical to or different from this, and $R^{14}$ denotes a group of the formula $-CO-R^{15}$, $-CO-NR^{16}R^{17}$ or $-SO_2R^{18}$, in which $R^{15}$ denotes hydroxyl or straight-chain or branched alkoxy having up to 6 carbon atoms, $R^{16}$ and $R^{17}$ are identical or different and have the abovementioned meaning of $R^{10}$ and $R^{11}$, or $R^{16}$ denotes hydrogen and $R^{17}$ denotes the group $-SO_2R^{18}$, $R^{18}$ denotes hydroxyl, straight-chain or branched alkoxy or alkyl each having up to 6 carbon atoms, amino or ($C_1-C_6$)-mono- or -dialkylamino or phenyl which can optionally be substituted up to 2 times by identical or different substituents from the group comprising halogen, trifluoromethyl and straight-chain or branched alkyl having up to 4 carbon atoms, or $R^{14}$ denotes a radical of the formula

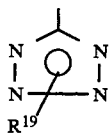

in which $R^{19}$ denotes hydrogen or straight-chain or branched alkyl having up to 8 carbon atoms, which is optionally substituted by straight-chain or branched acyl having up to 6 carbon atoms or denotes the triphenylmethyl group, and their salts.

The substituted biphenylpyridones according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts, for example, are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention, which have a free carboxyl group or a tetrazolyl radical. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can also exist in stereoisomeric forms which either behave as image and mirror image (enantiomers), or which do not behave as image and mirror image (diastereomers). The invention relates either to the enantiomers or diastereomers or to their respective mixtures. The racemic forms, like the diastereomers, can be separated in a known manner into the stereoisomerically uniform constituents [cf. E. L. Eliel, Stereochemistry of Carbon Compounds, McGraw Hill, 1962].

Heterocycle in general represents a 5- to 7-membered, preferably 5- to 6-membered, saturated or unsaturated ring which as heteroatoms can contain up to 2 oxygen, sulphur and/or nitrogen atoms. Preferred 5- and 6-membered rings are those having an oxygen, sulphur and/or up to 2 nitrogen atoms. The following may be mentioned as preferred: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl or tetrazolyl.

Preferred compounds of the general formula (I), are those in which $R^1$ represents straight-chain or branched alkyl, each having up to 8 carbon atoms, which is optionally substituted by cyclopropyl, cyclopentyl, cyclohexyl or hydroxyl or by straight-chain or branched alkoxy having up to 4 carbon atoms, or represents cyclopropyl, cyclopentyl, cyclohexyl, fluorine, chlorine, bromine or iodine, A represents a direct bond or the $-CH_2-$ group, or represents an oxygen or sulphur atom or the NH-group, $R^2$, $R^3$ and $R^4$ are identical or different and represent hydrogen, nitro, cyano, formyl, fluorine, chlorine, bromine or iodine, or represent straight-chain or branched alkyl, alkenyl, alkinyl, alkoxy, or alkylthio each having up to 6 carbon atoms, each of which is optionally substituted by hydroxyl, cyano, fluorine, chlorine, bromine, carboxyl, straight-chain or branched alkoxy, acyl or alkoxycarbonyl each having up to 4 carbon atoms, or by benzyl, phenyl, phenoxy, benzoyl or thienyl, where the cycles can in turn be substituted by trifluoromethoxy, trifluoromethyl, hydroxymethyl, fluorine, chlorine, bromine, iodine or by straight-chain or branched alkyl or alkoxy each having up to 6 carbon atoms, or represent straight-chain or branched acyl or alkoxycarbonyl each having up to 6 carbon atoms, phenoxycarbonyl, benzyloxycarbonyl or carboxyl or represent cyclopentenyl, cyclopropyl, cyclopentyl, cyclohexyl, thienyl, furyl, phenyl, phenoxy or phenylthio, each of which is optionally substituted up to 2 times by identical or different substituents from the group comprising fluorine, chlorine, bromine, iodine, trifluoromethyl, trifluoromethoxy and hydroxymethyl or by straight-chain or branched alkyl or alkoxy each having up to 4 carbon atoms, or represent tetrazoly, which is optionally substituted by methyl or a trityl group or represent a group of the formula

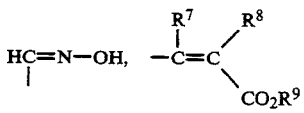

—NR$^{10}$R$^{11}$, —CO—NR$^{10}$—R$^{11}$ or —CH$_2$—OR$^{12}$, in which

R$^7$ denotes hydrogen or straight-chain or branched alkyl having up to 4 carbon atoms, R$^8$ denotes hydrogen or straight-chain or branched alkyl having up to 6 carbon atoms, which is optionally substituted by cyclopropyl, cyclohexyl, thienyl or phenyl, where the cycles are optionally substituted by hydroxyl, hydroxymethyl or straight-chain or branched alkyl or alkoxy each having up to 4 carbon atoms, R$^9$ denotes hydrogen, straight-chain or branched alkyl having up to 6 carbon atoms, R$^{10}$ and R$^{11}$ are identical or different and denote hydrogen, cyclopropyl, cyclopentyl, cyclohexyl or straight-chain or branched alkyl having up to 6 carbon atoms, which is optionally substituted by phenyl, R$^{12}$ denotes straight-chain or branched acyl having up to 6 carbon atoms or benzoyl, or —A—R$^1$ and R$^2$ together represent an alkylene chain having up to 5 carbon atoms, R$^5$ represents hydrogen, fluorine, chlorine, bromine, hydroxyl, trifluoromethyl, trifluoromethoxy or straight-chain or branched alkyl or alkoxy each having up to 4 carbon atoms, D represents a radical of the formula

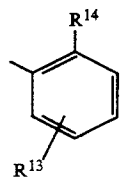

in which

R$^{13}$ has the abovementioned meaning of R$^5$ and is identical to or different from this and R$^{14}$ denotes a group of the formula —CO—R$^{15}$, —CO— NR$^{16}$R$^{17}$ or —SO$_2$R$^{18}$, in which R$^{15}$ denotes hydroxyl or straight-chain or branched alkoxy having up to 4 carbon atoms, R$^{16}$ and R$^{17}$ are identical or different and have the abovementioned meaning of R$^{10}$ and R$^{11}$ or R$^{16}$ denotes hydrogen and R$^{17}$ denotes the group —SO$_2$R$^{18}$, R$^{18}$ denotes straight-chain or branched alkyl having up to 4 carbon atoms or p-tolyl, or R$^{14}$ denotes a radical of the formula

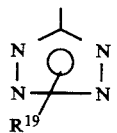

in which

R$^{19}$ denotes hydrogen or straight-chain or branched alkyl having up to 6 carbon atoms, which is optionally substituted by straight-chain or branched acyl having up to 4 carbon atoms or denotes the triphenylmethyl group, and their salts.

Particularly preferred compounds of the general formula (I) are those in which

R$^1$ represents straight-chain or branched alkyl having up to 6 carbon atoms, which is optionally substituted by cyclopropyl, hydroxyl or methoxy or represents cyclopropyl, chlorine or iodine, A represents a direct bond, the —CH$_2$ group, an oxygen or sulphur atom or the NH-group R$^2$, R$^3$ and R$^4$ are identical or different and represent hydrogen, nitro, cyano, formyl, fluorine, chlorine, bromine or iodine, or represent straight-chain or branched alkyl, alkenyl, alkinyl, alkoxy or alkylthio each having up to 4 carbon atoms, each of which is optionally substituted by hydroxyl, cyano or by straight-chain or branched alkoxy or alkoxycarbonyl each having up to 3 carbon atoms, benzyl, phenyl, phenoxy or benzoyl represent straight-chain or branched acyl or alkoxycarbonyl each having up to 4 carbon atoms, phenoxycarbonyl, benzyloxycarbonyl or carboxyl, or, represent cyclopropyl, cyclopentyl, thienyl, phenyl, phenoxy or phenylthio, each of which is optionally substituted by fluorine, chlorine, bromine, iodine or trifluoromethyl, or represent tetrazolyl which is optionally substituted by methyl or a trilyl group or represent a group of the formula

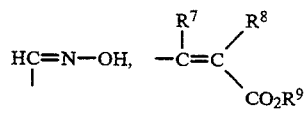

—CO—NR$^{10}$R$^{11}$ or —CH$_2$—OR$^{12}$, in which

R$^7$ denotes hydrogen or methyl,

R$^8$ denotes hydrogen or straight-chain or branched alkyl having up to 4 carbon atoms, which is optionally substituted by phenyl, which is in turn substituted by hydroxyl, hydroxymethyl or by straight-chain or branched alkyl or alkoxy each having up to 3 carbon atoms, R$^9$ denotes hydrogen or straight-chain or branched alkyl having up to 4 carbon atoms, R$^{10}$ and R$^{11}$ are identical or different and denote hydrogen, cyclopropyl, cyclopentyl or straight-chain or branched alkyl having up to 4 carbon atoms, which is optionally substituted by phenyl, R$^{12}$ denotes straight-chain or branched acyl having up to 4 carbon atoms or benzoyl, or —A—R$^1$ and R$^2$ together represent an alkylene chain having up to 4 carbon atoms R$^5$ represents hydrogen, fluorine, chlorine or methyl, D represents a radical of the formula

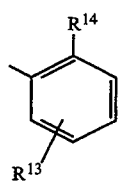

in which $R^{13}$ denotes hydrogen, and $R^{14}$ denotes a group of the formula —CO—$R^{15}$, —CO—$NR^{16}R^{17}$ or —$SO_2$—$R^{18}$, in which $R^{15}$ denotes hydroxyl or straight-chain or branched alkoxy having up to 3 carbon atoms, $R^{16}$ and $R^{17}$ are identical or different and have the abovementioned meaning of $R^{10}$ and $R^{11}$ or $R^{16}$ denotes hydrogen and $R^{17}$ denotes the group —$SO_2R^{18}$, in which $R^{18}$ denotes methyl or p-tolyl, or $R^{14}$ denotes the tetrazolyl radical of the formula

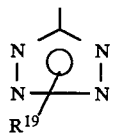

in which $R^{19}$ denotes hydrogen or straight-chain or branched alkyl having up to 4 carbon atoms, which is optionally substituted by straight-chain or branched acyl having up to 4 carbon atoms or denotes the triphenylmethyl group, and their salts.

Additionally, a process for the preparation of the compounds of the general formula (I) according to the invention has been found, characterised in that pyridones of the general formula (II)

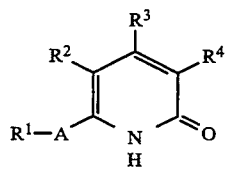

in which $R^1$, $R^2$, $R^4$ and A have the abovementioned meaning, are reacted with compounds of the general formula (III)

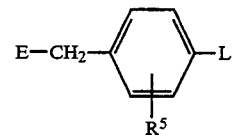

in which

E represents halogen, preferably bromine, and

L represents a radical of the formula

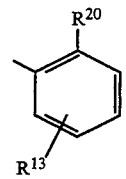

in which $R^{13}$ has the abovementioned meaning and $R^{20}$ denotes $C_1$-$C_4$-alkoxycarbonyl or a radical of the formula

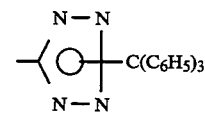

in inert solvents, in the presence of a base and if appropriate with the addition of a catalyst, and then in the case of the tetrazole radical the triphenylmethyl group is removed with acids in organic solvents and/or water according to customary conditions, and if appropriate in the case of the carbonyl radicals mentioned under the substituents $R^{14}$ and/or $R^{20}$, derivatised after hydrolysis of the respective esters, for example, by amidation or sulphonamidation according to customary methods, and, if appropriate, the substituents $R^2$, $R^3$, $R^4$, $R^5$, $R^{13}$ and $R^{19}$ are also varied according to the known methods.

The process according to the invention can be illustrated by way of example by the following reaction scheme:

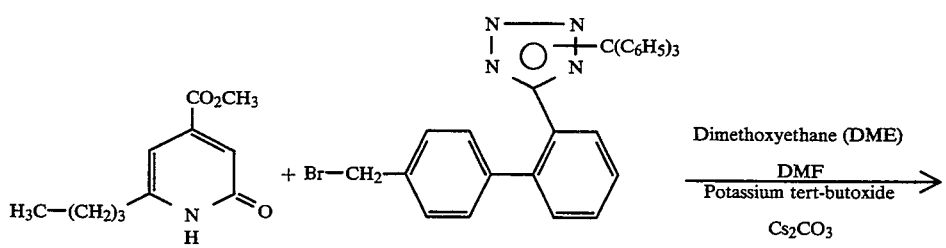

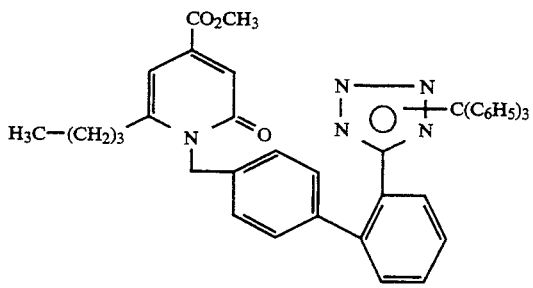 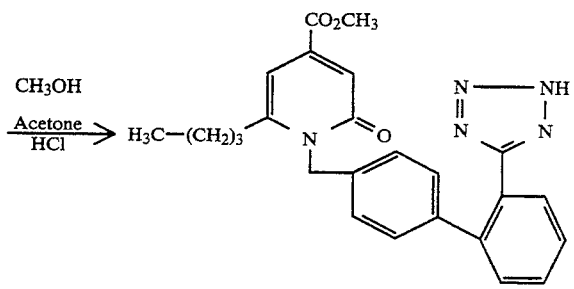

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide or dimethoxyethane, hexamethylphosphoramide, acetonitrile, acetone or nitromethane. It is also possible to use mixtures of the solvents mentioned. Tetrahydrofuran, acetone, dimethylformamide and dimethoxyethane are preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate or caesium carbonate, or alkali metal or alkaline earth metal alkoxides or amides such as sodium methoxide or potassium methoxide, sodium ethoxide or potassium ethoxide or potassium tert-butoxide, or lithium diisopropylamide (LDA) or organic amines (trialkyl($C_1$--$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals, such as sodium, or their hydrides such as sodium hydride. Potassium carbonate, sodium hydride, potassium tert-butoxide or caesium carbonate is preferred.

In general, the base is employed in an amount from 0.05 mol to 10 mol, preferably from 1 mol to 2 mol, relative to 1 mol of the compound of the formula (III).

The process according to the invention is in general carried out in a temperature range from −100° C. to +100° C., preferably from 0° C. to 80° C.

The process according to the invention is in general carried out at normal pressure. However, it is also possible to carry out the process at elevated pressure or at reduced pressure (for example in a range from 0.5 to 5 bar).

Suitable catalysts are potassium iodide or sodium iodine, preferably sodium iodide.

The triphenylmethyl group is removed with acetic acid or trifluoroacetic acid and water or one of the abovementioned alcohols or with aqueous hydrochloric acid in the presence of acetone or likewise with alcohols.

Removal in general takes place in a temperature range from 0° C. to 150° C., preferably from 20° C. to 100° C., and at normal pressure.

Alkylation in general takes place with alkylating agents such as, for example, ($C_1$-$C_6$)-alkyl halides, sulphonic acid esters or substituted or unsubstituted ($C_1$-$C_6$)-dialkyl- or ($C_1$-$C_6$) -diaryl sulphonates, preferably methyl iodide or dimethyl sulphate.

Alkylation in general takes place in one of the abovementioned solvents, preferably in dimethylformamide, in a temperature range from 0° C. to +70° C., preferably from 0° C. to +30° C., and at normal pressure.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogencarbonate, or alkali metal alkoxides such as sodium methoxide, sodium ethoxide, potassium methoxide, potassium ethoxide or potassium tert-butoxide. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The hydrolysis can optionally also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out with acids, such as, for example, hydrochloric acid or trifluoroacetic acid, in the presence of one of the abovementioned solvents and/or water or their mixtures, preferably with dioxane or tetrahydrofuran. The amidation and the sulphonamidation are in general carried out in one of the abovementioned solvents, preferably in tetrahydrofuran or dichloromethane.

The amidation and the sulphonamidation can optionally proceed via the activated stage of the acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from −20° C. to +80° C., preferably from −10° C. to +30° C., and at normal pressure.

Suitable bases for this in addition to the abovementioned bases are preferably triethylamine and/or dimethylaminopyridine, DBU or DABCO.

The base is employed in an amount from 0.5 mol to 10 mol, preferably from 1 mol to 2 mol, relative to 1 mol of the corresponding acid or ester.

Acid-binding agents which can be employed for the sulphonamidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[3.4.0]-non-5-ene (DBN) or 1,5-diazabicyclo[3.4.0]-undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. LEdis, J. Am. Chem. Soc. 95, 875 (1973); F. E. Frerman et al., J. Biol. Chem. 258, 7087–7093 (1983) and N. B. Benoton, K. Kluroda, 17, 197 (1981)].

The acid-binding agents and dehydrating reagents are in general employed in an amount from 0.5 to 3 mol, preferably from 1 to 1.5 mol, relative to 1 mol of the corresponding carboxylic acids.

The compounds of the general formula II are known in some cases or are new, and can in this case be prepared in analogy to known methods (cf., for example, DE 3,406,329 A1, R. P. Mariella, R. Stansfield, J. Am. Chem. Soc. 73, 1368 (1951) and O. Isler et al., Helv. Chim. Acta 38, 1033 (1955).

The compounds of the general formula (III) are known per se.

The above preparation processes are only given for clarification. The preparation of the compounds of the general formula (I) according to the invention is not restricted to these processes, and any modification of these processes can be used in the same way for the preparation.

The substituted biphenylpyridones according to the invention exhibit an unforeseeable, useful spectrum of pharmacological action.

The compounds according to the invention have a specific A II-antagonistic action, since they competitively or non-competitively inhibit the binding of angiotensin II to the receptors. They suppress the vasoconstricty and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, disorders of cerebral function, ischemic brain diseases, peripheral circulatory disorders, functional disorders of the kidney and adrenal gland, bronchospastic and vascular disorders of the respiratory passages, sodium retention and oedemas.

Investigation of the Inhibition of the Contraction Induced by Agonists

Rabbits of both sexes are stunned by a blow to the neck and bled out, or in some cases anaesthetised with Nembutal (about 60–80 mg/kg i.v.) and sacrificed by opening the thorax. The thorax aorta is removed, freed of adhering connective tissue, divided into 1.5 mm wide ring segments and individually transferred under an initial loading of about 3.5 g to 10 ml organ baths containing 95% $O_2$, 5% $CO_2$-aerated Krebs-Henseleit nutrient solution adjusted to 37° C. and of the following composition: 119 mmol/l of NaCl; 2.5 mmol/l of $CaCl_2 \times 2H_2O$; 1.2 mmol/l of $KH_2PO_4$; 10 mmol/l of glucose; 4.8 mmol/l of KCl; 1.4 mmol/l of $MgSO_4 \times 7 H_2O$ and 25 mmol/l of $NaHCO_3$.

The contractions are detected isometrically by Statham UC2 cells by means of bridge amplifiers (ifd Mülheim or DSM Aalen) and digitalised and analysed by means of an A/D converter (System 570, Keithley Munich). The agonist dose-response curves (DRC) are carried out hourly. With each DRC, 3 or 4 individual concentrations are applied to the baths at 4 min intervals. After the end of the DRC and subsequent washing-out cycles (16 times, in each case about 5 sec/min with the abovementioned nutrient solution), a 28-minute resting or incubation phase follows, in the course of which the contractions as a rule reach the starting value again.

The height of the 3rd DRC, in the normal case, is used as a reference quantity for the assessment of the test substance to be investigated in other passages, which is applied to the baths in the following DRCs in increasing dosage in each case at the start of the incubation time. Each aorta ring is in this way stimulated for the whole day, always with the same agonist.

| Agonists and their standard concentrations (application volume per individual dose = 100 μl): | | |
|---|---|---|
| KCl | 22.7; 32.7; 42.7; 52.7 | mmol/l |
| Noradrenalin | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

For the calculation of the $IC_{50}$ (concentration at which the substance to be investigated causes a 50% inhibition), the effect is in each case based on the 3rd=sub-maximal agonist concentration.

The compounds according to the invention inhibit the contraction of the isolated rabbit aorta induced by angiotensin II in a dose-dependent manner. The contraction induced by potassium depolarisation or other agonists was not inhibited or only weakly inhibited at high concentrations.

TABLE A

Inhibition of the vascular contraction of isolated aorta rings of rabbits in vitro
$IC_{50}$ (g/ml) for contractions induced by: AII

| Ex. No.: | $IC_{50}$ [nM] |
|---|---|
| XCII | 120 |
| LXXVIII | 34 |
| XLIII | 39 |
| XLV | 3.7 |
| LIV | 13 |
| XXXIII | 7.3 |
| LXXIII | 8.6 |

Blood Pressure Measurements on the Angiotensin II-Infused Rat

Male Wistar rats (Moellegaard, Copenhagen, Denmark) having a body weight of 300–350 g are anaesthetised with thiopental (100 mg/kg i.p.). After tracheotomy, one catheter is inserted in the femoral artery for blood pressure measurement and one catheter is inserted in the femoral veins for angiotensin II infusion and one catheter for substance administration. After administration of the ganglionic blocker pentolinium (5 mg/kg i.v.), angiotensin II infusion (0.3 µg/kg/min) is started. As soon as the blood pressure values have reached a stable plateau, the test substances are administered either intravenously or orally as a suspension or solution in 0.5% tylose. The blood pressure changes under the influence of the substance are indicated in the Table as average values ± SEM.

Ex. No. I: 0.3 mg/kg p.o. Blood pressure decrease >50 mm Hg

Determination of the Antihypertensive Activity in Conscious Hypertensive Rats

The oral antihypertensive activity of the compounds according to the invention was tested on conscious rats having surgically induced unilateral renal arterial stenosis. To do this, the right renal artery was constricted with a silver clip of 0.18 mm internal width. In this form of hypertension, the plasma renin activity in the first six weeks after intervention is increased. The arterial blood pressure of these animals was measured in a bloodless manner at defined time intervals after substance administration using the "tail cuff". The substances to be tested were administered intragastrically ("orally") by stomach tube in various doses suspended in a tylose suspension. The compounds according to the invention decreased the arterial blood pressure of high pressure rats at a clinically relevant dosage.

Additionally, the compounds according to the invention inhibit the specific binding of radioactive angiotensin II in a concentration-dependent manner.

Interaction of the Compounds According to the Invention With the Angiotensin II Receptor on Membrane Fractions of the Adrenal Cortex (Cattle)

Adrenal cortices of cattle (ACC), which have been freshly removed and carefully freed of gland medulla, are comminuted in sucrose solution (0.32M) with the aid of an Ultra-Turrax (Janke & Kunkel, Staufen i.B.) to give a coarse membrane homogenate and partially purified in two centrifugation steps to give membrane fractions. The investigations of receptor binding were carried out on partially purified membrane fractions of bovine ACC using radioactive angiotensin II in an assay volume of 0.25 ml, which in detail contains the partially purified membranes (50–80 µg), $^3$H-angiotensin II (3–5 nM), test buffer solution (50 mM tris, pH 7.2, 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ and $IC_{50}$ values (Ki: $IC_{50}$ values corrected for the radioactivity used; $IC_{50}$ values: concentration at which the substance to be investigated causes a 50% inhibition of the specific binding of the radioligand).

| Ex. No.: | $K_i$ [nM] |
|---|---|
| XXXIV | >10,000 |
| XLVII | 220 |
| XCIV | 42 |
| LV | 15 |
| LVI | 9 |
| LXXXII | 79 |

Investigation of Inhibition of the Proliferation of Smooth Muscle Cells by the Compounds According to the Invention To determine the antiproliferative action of the compounds, smooth muscle cells are used which have been obtained from the aorta of rats by the media explant technique [R. Ross, J. Cell. Biol. 50, 172, 1971]. The cells are inoculated into suitable culture dishes, as a rule 24-hole plates, and cultured in 5% $CO_2$ at 37° C. for 2–3 days in medium 199 containing 7.5% FCS and 7.5% NCS, 2 mM L-glutamine and 15 mM HEPES, pH 7.4. The cells are then synchronised by serum withdrawal for 2–3 days and then stimulated into growth with AII, serum or other factors. Test compounds are simultaneously added. After 16–20 hours, 1 µCi of $^3$H-thymidine is added and after a further 4 hours the incorporation of this substance into the TCA-precipitatable DNA of the cells is determined. The novel active substances can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active substances with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active substance using suitable liquid excipient materials can be employed.

In general, it has proved advantageous on intravenous administration to administer amounts of about 0.01 to 1 mg/kg, preferably of about 0.01 to 0.5 mg/kg of body weight, to achieve effective results, and in the case of oral administration the dosage is about 0.01 to 20 mg/kg, preferably 0.1 to 10 mg/kg of body weight.

In spite of this, it may sometimes be necessary to depart from the amounts mentioned, in particular depending on the body weight or on the type of administration route, on individual behaviour towards the medicament, the manner of its formulation and the time or interval at which administration takes place. Thus, in some cases it may be sufficient to manage with less than the abovementioned minimum amount, while in other cases the abovementioned limit must be exceeded. In the case of the administration of relatively large amounts, it may be advisable to divide these into several individual doses over the course of the day.

STARTING COMPOUNDS

Example 1

6-Butyl-4-methoxycarbonyl-2-oxo-1,2-dihydropyridine

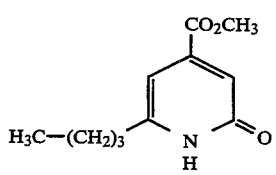

12.5 ml (0.17 mol) of thionyl chloride are added dropwise with ice-cooling to a suspension of 29.25 g (0.15 mol) of 6-butyl-2-oxo-1,2-dihydro-isonicotinic acid in 200 ml of methanol and the mixture is stirred overnight at room temperature. It is concentrated to dryness and the residue is chromatographed on 450 g of silica gel (230–400 mesh) using dichloromethane→dichloromethane/methanol 10:1. 29.6 g (94%) of colourless crystals m.p.: 106° C. crystallise from dichloromethane, ether and petroleum ether.

The examples shown in Table 1 are prepared in analogy to the procedure of Example 1:

TABLE 1

[Structure: pyridinone with $CO_2R$ at 4-position, $R^1$ at 6-position, N-H, C=O]

Starting compounds
[Structure: pyridinone with $CO_2H$ at 4-position, $R^1$ at 6-position, N-H, C=O]

| Ex. No. | $R^1$ | R | m.p. [°C.] | Yield (% of theory) | $R^1$ |
|---|---|---|---|---|---|
| 2 | -n-$C_4H_9$* | —$C_2H_5$ | 98 | 97 | -n-$C_4H_9$ |
| 3 | -n-$C_4H_9$* | —$CH(CH_3)_2$ | 127 | 86 | -n-$C_4H_9$ |
| 4 | -n-$C_3H_7$ | —$CH_3$ | 144 | 88 | -n-$C_3H_7$ |
| 5 | -n-$C_3H_7$* | —$C_2H_5$ | 129 | 93 | -n-$C_3H_7$ |
| 6 | —$C_2H_5$ | —$CH_3$ | 192 | 85 | —$C_2H_5$ |
| 7 | ▷— | —$CH_3$ | 191 | 35 | ▷— |
| 8 | -n-$C_5H_{11}$ | —$CH_3$ | 100 | 87 | -n-$C_5H_{11}$ |
| 9 | —$CH_3$* | —$C_2H_5$ | 184–186 | | —$CH_3$ |

*In a modification to the procedure of Example 1, ethanol or isopropanol is used instead of methanol and the mixture is stirred overnight at 50° C.

Example 10

6-Butyl-2-oxo-1,2-dihydro-pyridine

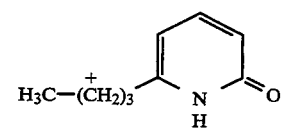

4.9 g (25 mmol) of 6-butyl-2-oxo-1,2-dihydro-isonicotinic acid are boiled under reflux (237° C.) for 1.5 h with 1.79 g (12.5 mmol) of copper (I) oxide in 50 ml of quinoline. After filtering off, the volatile constituents are removed by distillation in vacuo (110° C. at 17 mbar, then 67° C. at 9 mbar). The residue is chromatographed twice on silica gel using dichloromethane/methanol (40:1)→(20:1) and the product is stirred in petroleum ether.

Yield: 1.95 g (52%) of brownish crystals, m.p.: 68° C.

Example 11

6-Butyl-4-benzyloxycarbonyl-2-oxo-1,2-dihydropyridine

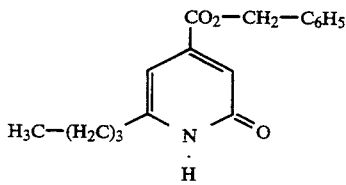

13.3 g (123 mmol) of benzyl alcohol and 4.7 g (31 mmol) of hydroxybenzotriazole are added to a solution of 6.0 g (31 mmol) of 6-butyl-2-oxo-1,2-dihydro-isonicotinic acid in 100 ml of DMF. The resulting clear solution is cooled to 0° C. followed by the addition of 7.0 g (34 mmol) of dicyclohexylcarbodiimide and 4.2 ml (31 mmol) of triethylamine. The mixture is allowed to thaw at 20° C., stirred for a further 2 hours and subjected to aqueous work-up. 6.8 g (77%) of theory of the title compound are obtained.

m.p.: 139° C.

Example 12

6-Propyl-2-oxo-1,2-dihydropyridine

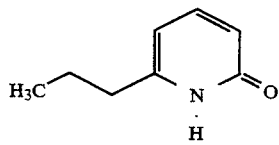

Analogously to the process of Example 10, the title compound of m.p. 89°–90° C. is obtained in 71% of theory.

Example 13

6-Butyl-4-carbamoyl-2-oxo-1,2-dihydropyridine

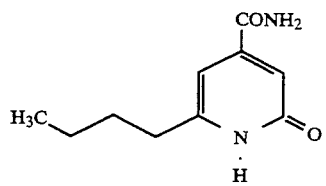

3 g (14.3 mmol) of the compound from Example 1 are heated for a few minutes in 10 ml of ethanol and 20 ml of conc. ammonia. A further 5 ml of conc. ammonia are then added three times each and the mixture is again briefly heated to boiling. After cooling, the precipitate is filtered off with suction and dried over $P_2O_5$ in vacuo.

Yield: 1.19 g (43%) of colourless crystals m.p. from 290° C. (decomposition).

Example 14

4-Carbamoyl-2-oxo-6-propyl-1,2-dihydropyridine

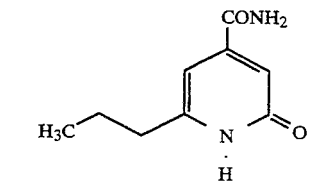

In analogy to the procedure of Example 13, the title compound is obtained from the compound from Example 4 in a yield of 66% of theory (colourless crystals, m.p.: >280° C.).

Example 15

4-Benzylcarbamoyl-6-butyl-2-oxo-1,2-dihydropyridine

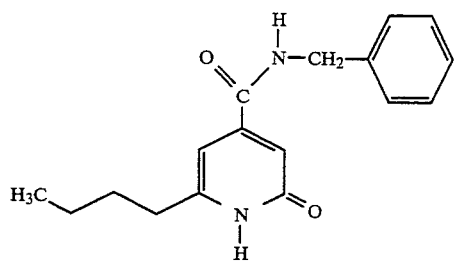

Analogously to the process from Example 11, 2 mol equivalents of benzylamine being employed instead of benzyl alcohol and triethylamine, the title compound, colourless crystals of m.p 177° C. is obtained in 47% yield.

Example 16

4-Benzylcarbamoyl-2-oxo-6-propyl-1,2-dihydro-pyridine

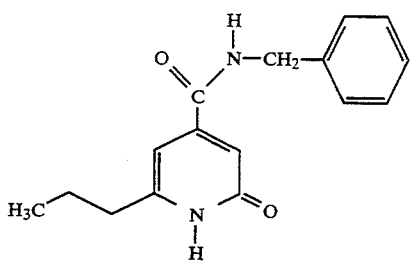

Analogously to the process from Example 15, the title compound is obtained from 2-oxo-6-propyl-1,2-dihydroisonicotinic acid in 44% yield (colourless crystals, m.p. 210° C.).

Example 17

3-Cyano-4,6-dipropyl-2-oxo-1,2-dihydropyridine

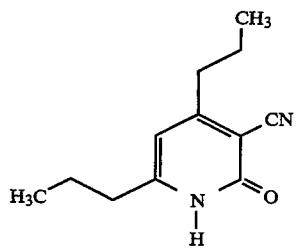

15.6 g (0.1 mol) of 4,6-nonadione are heated under reflux for 4 hours with 8.4 g (0.1 mol) of cyanacetamide and 13.8 g (0.1 mol) of potassium carbonate in 100 ml of acetone. The acetone is stripped off in vacuo, the residue is suspended in 250 ml of water and acidified to pH 1 to 2 with conc. hydrochloric acid, and the precipitate is filtered off with suction, washed with water and dried over $P_2O_5$ in vacuo.

Yield: 18.2 g (89%) of colourless crystals, m.p.: 148° C.

Example 18

6-Butyl-3-cyano-4-methyl-2-oxo-1,2-dihydropyridine

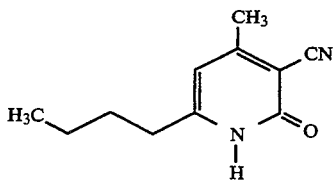

Analogously to the procedure for Example 17, the title compound is obtained from 2,4-octanedione in 94% yield. m.p.: 144° to 148° C. The product contains about 15% of isomeric 4-butyl-3-cyano-6-methyl-pyrid-2(1H) one as an impurity.

Example 19

4,6-Dipropyl-2-oxo-1,2-dihydropyridine

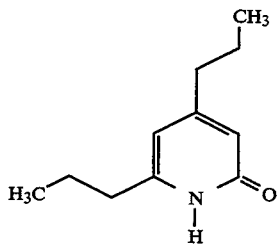

13.1 g (64 mmol) of the compound from Example 17 are heated under reflux for 4 hours in 22 ml of water and 22 ml of conc. sulphuric acid. A pH of about 6 is established with $Na_2CO_3$, the precipitated oil is taken up in ethyl acetate, and the organic phase is washed with satd. sodium chloride solution and dried over $Na_2SO_4$. After stripping off the solvent, the residue is dried in a high vacuum.

Yield: 9.5 g (83%) of yellowish solid of m.p. 62° C.

Example 20

6-Butyl-4-methyl-2-oxo-1,2-dihydropyridine

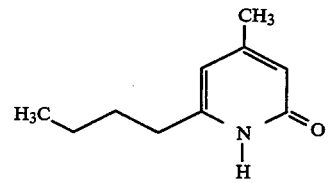

Analogously to the preceding example, the title compound is obtained from the compound from Example 18. m.p. 95° C. The product contains about 10% of isomeric 4-butyl-6-methyl-pyrid-2(1H)-one as an impurity.

Example 21

4-Hydroxymethyl-6-propyl-2-oxo-1,2-dihydropyridine

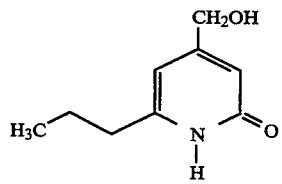

27.8 ml and, after 1 hour at room temperature, a further 27.8 ml of a 1M solution of $BH_3$ in THF are added dropwise at 0° C. to a suspension of 3.0 g (16.6 mmol) of 2-oxo-6-propyl-1,2-dihydroisonicotinic acid and the mixture is stirred for a further hour at room temperature. 66.8 ml of 1N hydrochloric acid and 100 ml of water are added to the now clear solution, and it is stirred at room temperature for 1 hour and extracted three times with 75 ml of ethyl acetate each time. The organic phase is discarded, the aqueous phase is adjusted to a pH of about 7 with satd. $NaHCO_3$ solution and the deposited precipitate is filtered off with suction. The aqueous filtrate is concentrated to dryness in a rotary evaporator and recrystallised from about 80 ml of water together with the first precipitate. 1.28 g (46%) of colourless crystals of m.p. 167° C. are obtained.

Example 22

2-Benzoyloxy-4-benzoyloxymethyl-6-propyl-pyridine

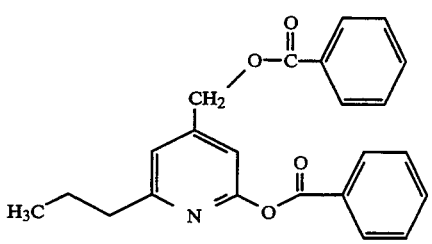

3.1 ml (22.6 mmol) of triethylamine, 0.28 g (2.3 mmol) of 4-dimethylaminopyridine and 1.3 ml (11.3 mmol) of benzoyl chloride are added at about 10° C. to a suspension of 1.26 g (7.5 mmol) of the compound from Example 21 in 40 ml of THF and the mixture is stirred at room temperature for 3 hours. 50 ml of water are then added, the mixture is extracted three times with 30 ml of ethyl acetate each time, and the combined organic phases are washed with satd. NaHCO₃ solution, citric acid solution and NaHCO₃ solution, dried over Na₂SO₄ and concentrated. The residue is chromatographed on 40 g of silica gel (230–400 mesh) using dichloromethane/ethyl acetate 100:1→20:1.

Yield: 1.67 g (59%) of colourless solid $R_f$ 0.73 (dichloromethane/ethyl acetate 20:1).

Example 23

6-Propyl-3,5-diethoxycarbonyl-2-oxo-1,2-dihydropyridine

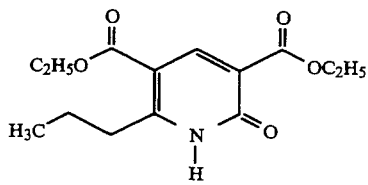

62.8 g (0.4 mol) of ethyl 3-amino-hex-2-en-oate and 86.4 g (0.4 mol) of diethyl ethoxymethylenemalonate are stirred at 100° C. for 40 hours. The mixture is cooled to 20° C. and the solid is filtered off with suction and recrystallised from ethanol.

Yield: 36.2 g, 32.2% of theory ¹H-NMR (CDCl₃) δ=1.05 (t, 3H), 1.4 (dt, 6H), 1.8 (m, 2H), 3.15 (t, 2H), 4.35 (m, 4H), 8.8 (s, 1H), 13.1 (s, 1H) ppm.

Example 24

5-Ethoxycarbonyl-3-methoxycarbonyl-2-oxo-4-phenyl-6-propyl-1,2,3,4-tetrahydropyridine

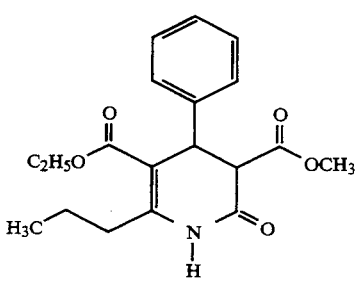

26.2 g (0.128 mol) of dimethyl benzylidenemalonate and 20.1 g (0.128 mol) of ethyl-3-amino-hex-2-en-oate are stirred at 140° C. for 3 days with a spatula tip full of sodium ethoxide. The mixture is chromatographed on silica gel using methylene chloride and crystallised from petroleum ether.

Yield: 6.7 g, 15% of theory. $R_f$=0.47 ethyl acetate:petroleum ether 1:1.

Example 25

5-Ethoxycarbonyl-3-methoxycarbonyl-2-oxo-4-phenyl-6-propyl-1,2-dihydropyridine

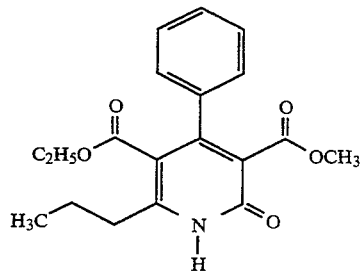

5.7 g (16.5 mmol) of the compound from Example 24 and 18.0 g (33 mmol) of ceric ammonium nitrate are stirred overnight at 20° C. in 100 ml of acetonitrile/50 ml of water, the acetonitrile is removed by distillation, the aqueous phase is washed with methylene chloride, and the organic phase is washed with water, dried (sodium sulphate) and concentrated. Yield 5.0 g, 88% of theory.

$R_f$=0.19 ethyl acetate/petroleum ether 1:1.

Example 26

5-Ethoxycarbonyl-2-oxo-4-phenyl-6-propyl-1,2,3,4-tetrahydropyridine

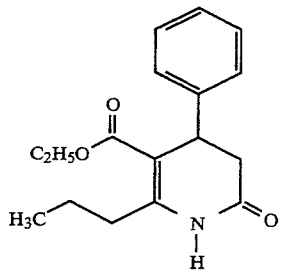

8.7 g (25 mmol) of the compound from Example 24 and 1.5 g of sodium chloride are stirred overnight at 180° C. in 25 ml of DMSO/1.2 ml of water. The mixture is cooled to 20° C., poured into water and washed with ethyl acetate. The organic phase is washed with water and dried over sodium sulphate.

Yield: 3.9 g (67% of theory) $R_f$=0.45 petroleum ether/ethyl acetate 2:1.

Example 27

5-Ethoxycarbonyl-2-oxo-4-phenyl-6-propyl-1,2-dihydropyridine

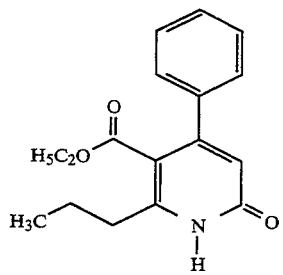

Analogously to the process from Example 25, 6.5 g of the compound from Example 26 are reacted to give 3.6 g of the title compound. Yield: 56% of theory R$_f$=0.21 petroleum ether/ethyl acetate 1:1.

Example 28

6-Butyl-3,4-bis-ethoxycarbonyl-2-oxo-1,2-dihydropyridine

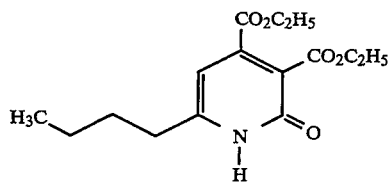

10 g (50 mmol) of ethyl 2,4-dioxo-octanecarboxylate, 5.65 g (50 mmol) of ethyl cyanoacetate and 5 g (50 mmol) of triethylamine are heated under reflux overnight in 100 ml of ethanol.

The solvent is removed by distillation, the residue is dissolved in methylene chloride, the solution is washed with dilute hydrochloric acid and water and the organic phase is dried over sodium sulphate. The mixture is chromatographed on silica gel using methylene chloride/methanol gradients.

Yield: 8.8 g (60% of theory). MS (DCI) 296 (M+H).

Example 29

6-Ethyl-3,5-diiodo-4-methoxycarbonyl-2-oxo-1,2-dihydropyridine

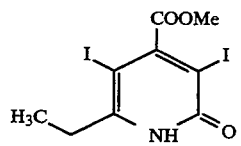

A solution of 6-ethyl-3,5-diiodo-4-carboxy-2-oxo-1,2-dihydropyridine (0.10 g; 0.24 mmol) in thionyl chloride (1.1 ml) is heated at 80° C. for 3 h, then concentrated and boiled under reflux for 1 h after addition of methanol (5 ml). Concentration, partition of the residue between ethyl acetate and sodium bicarbonate solution and drying of the organic phase with saturated sodium chloride solution and sodium sulphate gives, after concentration, 0.10 g of a solid (96% of theory).

R$_f$=0.43 (methylene chloride:methanol:formic acid=10:1:0.1). MS(EI): 433 (100%; M)

Example 30

Methyl 6-butyl-3,5-diiodo-4-methoxycarbonyl-2-oxo-1,2-dihydropyridine-4-carboxylate

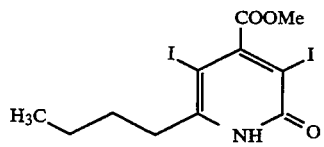

A solution of 6-butyl-1,2-dihydro-3,5-diiodo-2-oxopyridine-4-carboxylic acid (50 g; 0.11 mol) in dimethylformamide (250 ml) is treated at 0° C. with potassium carbonate (17 g; 0.12 mol) and a solution of methyl iodide (6.7 ml; 0.11 mol) in dimethylformamide (50 ml) and then stirred at room temperature overnight. The reaction solution is concentrated, the residue is taken up in ethyl acetate and the solution is washed with potassium hydrogensulphate solution, sodium carbonate solution and saturated sodium chloride solution. Drying and concentration of the organic phase and silica gel chromatography (methylene chloride: ethyl acetate=10:1) yields 30 g of a yellow solid (58% of theory).

R$_f$=0.47 (methylene chloride: ethyl acetate=20:1). MS (DCI): 336 (100%, M+H)

Example 31

6-Butyl-3,5-diiodo-4-methoxycarbonyl-2-oxo-3-(2-phenylethenyl)-1,2-dihydropyridine

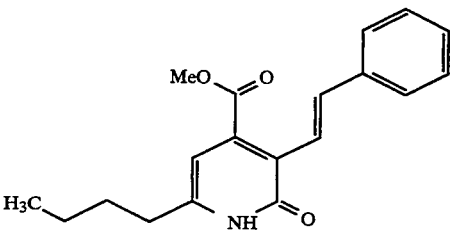

A solution of the compound from Example 30 (3.0 g; 6.5 mmol) in N-methylpyrrolidin-2-one is treated under argon with palladium (II) acetate (15 mg; 0.065 mol), tributylamine (1.6 ml; 6.5 mmol) and styrene (0.82 ml; 7.2 mmol) and heated at 80° C. for 48 h. Tributylstannane (5.3 ml; 20 mmol) is then added, the mixture is stirred overnight at 80° C. tetrakis(triphenylphosphine)-palladium (1.2 g; 1.0 mmol) is added and the mixture is again stirred overnight at 80° C. Concentration, partition of the residue between ethyl acetate and potassium hydrogensulphate solution, drying and concentration of the organic phase, and silica gel chromatography (hexane:ethyl acetate=3:1) give 0.49 g of a yellow resin (23% of theory).

R$_f$=0.20 (hexane:ethyl acetate=3:1). MS(DCI): 312 (100%, M+H)

The compounds shown in Table 2 are prepared analogously to the process of Example 17:

TABLE 2

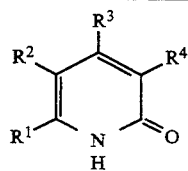

| Ex. No. | R¹ | R² | R³ | R⁴ | m.p. [°C.] | Starting material |
|---|---|---|---|---|---|---|
| 32 | CH₃OCH₂— | H | —COOCH₃ | —CN | 200–203° (dec.) | CH₃OCH₂C(O)—CH₂C(O)—COOCH₃ |
| 33 | (CH₃)₂CH— | H | —COOCH₂CH₃ | —CN | 191 | (CH₃)₂CH—CCH₂C(O)—COOCH₂CH₃ |

The compounds in Table 3 are prepared in two steps in analogy to the preparation procedures of Examples 1 and 19.

TABLE 3

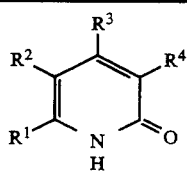

| Ex. No. | R¹ | R² | R³ | R⁴ | m.p. [°C.] | Starting material/ Example No. |
|---|---|---|---|---|---|---|
| 34 | CH₃OCH₂— | H | —COOCH₃ | H | 165 | 32 |
| 35 | (CH₃)₂CH— | H | —COOCH₃ | H | 188 | 33 |

The following compounds are prepared by the processes given there.

TABLE 4

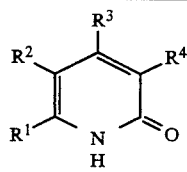

| Ex. No. | R¹ | R² | R³ | R⁴ | Yield [% of theory] | R_f* | Starting material**/ Ex. No. | Process analogous to Ex. |
|---|---|---|---|---|---|---|---|---|
| 36 | n-C₃H₇ | —COOCH₂CH₃ | H | —COOH | 55 | 0.15¹⁾ | 23 | CV |
| 37 | n-C₃H₇ | —COOCH₂CH₃ | H | H | 28 | 0.46¹⁾ | 36 | 10 |
| 38 | n-C₄H₉ | —H | H | —COOH | 86 | 0.45¹⁾ | 2) | conc. HCl/100* |
| 39 | n-C₄H₉ | —H | H | —COOCH₃ | 95 | 0.64¹⁾ | 38 | 1 |

*solvent mixtures:
¹⁾Dichloromethane/methanol (20:1)
**starting material
²⁾3-cyano-6-butyl-pyrid-2(1H)-one

Example 40

6-Butyl-4-cyano-2-oxo-1,2-dihydropyridine

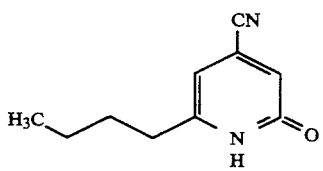

To a suspension of the compound from example 13 (4.6 g, 24 mmole) in 50 ml of dioxane is added at 10° C. pyridine (3.8 ml) 48 mole) and dropwise trifluoroacetic acid anhydride and the mixture stirred for 6 h at r.t. 150 ml of dichloromethane are added, the precipitate is removed by filtration, the filtrate washed with water and borine, dried over Na₂SO₄ and evaporated to dryness. The residue is treated with ether and the crystals are collected by suction.

Yield 2.03 g (52%) colourless crystals of m.p. 273° C.

Example 41

6-Butyl-2-oxo-4-(tetrazol-5-yl)1,2-dihydropyridine

The compound of example 40 (1.6 g; 9.7 mmol) is stirred together with triethylammonium chloride (6.97 g (50.7 mmol) and sodiumazide in 100 ml of DMF at a flask temperature of about 130° C. behind a shield. The mixture is evaporated not completely to dryness, 400 g of ice are added and the pH adjusted to 1.2 with 1N sulfuric acid. It is extracted three times with 400 ml ethylacetate each, the combined organic phases are dried over Na₂SO₄ and evaporated. The residue is crystallized from dichloromethane, ether, petrolether.

Yield: 1.95 g (90%) colourless crystals m.p. 227° C.

Example 42

6-Butyl-2-oxo-4(N-triphenylmethyl-tetrazol-5-yl) 1,2-dihydropyridine

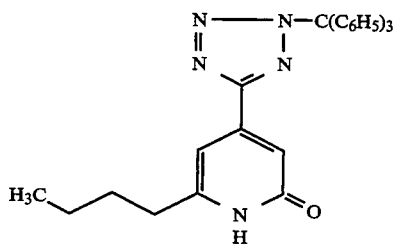

The compound of example 41 (1.0 g, 4.6 mmole) is dissolved in 30 ml of dichloromethane and refluxed together with triphenylmethylchloride (1.46 g, 5.4 mmole) and triethylamine 0.8 ml, 5.8 mmoles) for 2 h. After washing with water and borine it is evaporated to dryness and the residue crystallized from dichloromethane/ether/petrolether.

Yield: 1.73 g (82%) colourless crystals, which decompose at 208° C.

PREPARATION EXAMPLES

Example I

6-Butyl-4-methoxycarbonyl-2-oxo-1-{[2'-(N-triphenyl-methyl-tetrazol-5-yl)biphenyl-4-yl]methyl}-1,2-dihydropyridine

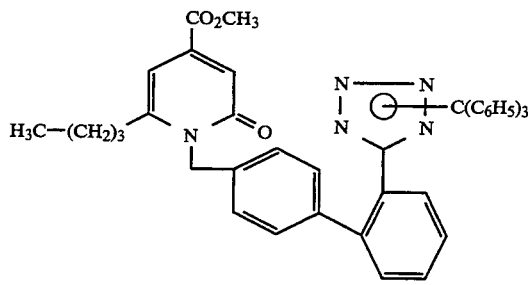

Process A 20.92 g (0.1 mol) of the compound from Example 1 are dissolved in 200 ml of DMF, treated in portions with 13.5 g of potassium tertiary butoxide and stirred at RT for 10 min. A solution of 55.75 g (0.1 mol) of N-triphenylmethyl-5-[2-(4'-bromomethylbiphenyl)]tetrazole in 200 ml of DMF is then added dropwise and the mixture is stirred at RT overnight. 500 ml of water are added dropwise, the mixture is extracted three times with 300 ml of ethyl acetate each time, and the combined organic phases are dried over sodium sulphate and concentrated. The residue is chromatographed on 450 g of silica gel (250–400 mesh) using a gradient of petroleum ether/ethyl acetate (5:1)→(1:2).

Yield: 9.69 g (14%) of colourless foam $R_f$: 0.3 petroleum ether/ethyl acetate (2:1)

Process B 61.1 g (0.188 mol) of caesium carbonate are added to a solution of 31.4 g (0.15 mmol) of the compound from Example 1 in 600 ml of dimethoxyethane, the mixture is stirred at room temperature for 15 minutes, then 100.4 g (0.18 mol) of N-triphenylmethyl-5-[2-(4'-bromomethylbiphenyl)tetrazole are added, and the mixture is stirred overnight at room temperature and boiled for 3 hours under reflux.

The reaction mixture is then partitioned between water and ethyl acetate (about 0.8 l each), and the organic phase is washed with satd. sodium chloride solution, dried over $Na_2SO_4$ and concentrated. The residue is filtered through 2 kg of silica gel (230–400 mesh) using petroleum ether/ethyl acetate (5:1)→(1:1).

Yield: 39.8 g (38.6%) of yellowish amorphous solid $R_f$: 0.3 petroleum ether/ethyl acetate (2:1).

About 70 g of crude 6-butyl-4-methoxycarbonyl-2-{[2'-(N-triphenylmethyl-tetrazol-5-yl)biphenyl-4-yl]methoxypyridine are isolated as a by-product.

$R_f$: 0.78 petroleum ether/ethyl acetate (2:1).

The compounds shown in Table I are obtained in analogy to processes A and B of the compound from Example I:

TABLE I

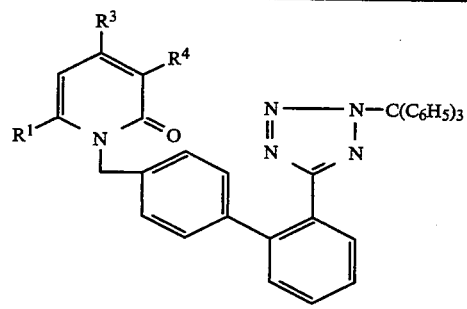

| Ex. No. | R1 | R3 | R4 | Yield (% of theory) | $R_f$* | Starting material/ process A/B |
|---|---|---|---|---|---|---|
| II | -n-$C_4H_9$ | H | H | 14 | 0.16[1] | 10/A |
| III | —$C_2H_5$ | —$C_2H_5$ | CN | 20 | 0.12[1] | A |
| IV | -n-$C_4H_9$ | —$CO_2C_2H_5$ | H | 16 | 0.40[1] | 2/B |
| V | -n-$C_4H_9$ | —$CO_2CH(CH_3)_2$ | H | 34 | 0.48[1] | 3/B |
| VI | -n-$C_3H_7$ | —$CO_2CH_3$ | H | 26 | 0.24[1] | 4/B |
| VII | -n-$C_3H_7$ | —$CO_2C_2H_5$ | H | 25 | 0.29[1] | 5/B |
| VIII | —$C_2H_5$ | —$CO_2CH_3$ | H | 25 | 0.15[1] | 6/B |

TABLE I-continued

| Ex. No. | R1 | R3 | R4 | Yield (% of theory) | R_f* | Starting material/ process A/B |
|---|---|---|---|---|---|---|
| IX | ◁ | —CO$_2$CH$_3$ | H | 39 | 0.12[1] | 7/B |
| X | -n-C$_5$H$_{11}$ | —CO$_2$CH$_3$ | H | 33 | 0.29[1] | 8/B |
| XI | —CH$_3$ | —CO$_2$C$_2$H$_5$ | H | 41 | 0.18[1] | 9/B |
| XII | -n-C$_4$H$_9$ | —CO$_2$—CH$_2$C$_6$H$_5$ | H | 30 | 0.40[1] | 11/B |
| XIII | -n-C$_3$H$_7$ | H | H | 13 | 0.08[1] | 12/B |
| XIV | -n-C$_4$H$_9$ | —CONH$_2$ | H | 20 | 0.33[2] | 13/B |
| XV | -n-C$_4$H$_9$ | —CONH—CH$_2$C$_6$H$_5$ | H | 27 | 0.11[1] | 15/B |
| XVI | -n-C$_4$H$_9$ | —CO$_2$C$_2$H$_5$ | CN | 19 | 0.19[1] | B ⟶ |
| XVII | -n-C$_3$H$_7$ | —CO$_2$C$_2$H$_5$ | CN | 21 | 0.07[1] | B |
| XVIII | —C$_2$H$_5$ | —CO$_2$C$_2$H$_5$ | CN | 14 | 0.11[1] | B |
| XIX | ◁ | —CO$_2$C$_2$H$_5$ | CN | 5 | 0.15[1] | B |
| XX | -n-C$_3$H$_7$ | H | CN | 10 | 0.16[1] | **A |
| XXI | -n-C$_3$H$_7$ | -n-C$_3$H$_7$ | CN | 44 | 0.2[1] | 17/B |
| XXII | -n-C$_4$H$_9$ | —CH$_3$ | CN | 22 | 0.19[1] | 18/B |
| XXIII | -n-C$_3$H$_7$ | -n-C$_3$H$_7$ | H | 30 | 0.17[1] | 19/B |
| XXIV | -n-C$_4$H$_9$ | —CH$_3$ | H | 23 | 0.14[1] | 20/B |
| XXV | -n-C$_3$H$_7$ | —CH$_2$O—CO—C$_6$H$_5$ | H | 13 | 0.21[1] | 22/B |
| XXVI | -n-C$_3$H$_7$ | —CONH$_2$ | H | 14 | 0.5[2] | 14/B |
| XXVII | -n-C$_3$H$_7$ | —CO$_2$—NHCH$_2$—C$_6$H$_5$ | H | 16 | 0.16[3] | 16/B |

*eluent mixture:
[1] petroleum ether/ethyl acetate 2:1
[2] dichloromethane/methanol 10:1
[3] petroleum ether/ethyl acetate 1:1
**Starting Material: 3-cyano-6-propyl-pyrid-2-on

Example XXVIII

6-Butyl-4-hydroxymethyl-2-oxo-1{[2'-(N-triphenyl-methyl-tetrazol-5-yl)biphenyl-4-yl]methyl}1,2-dihydropyridine

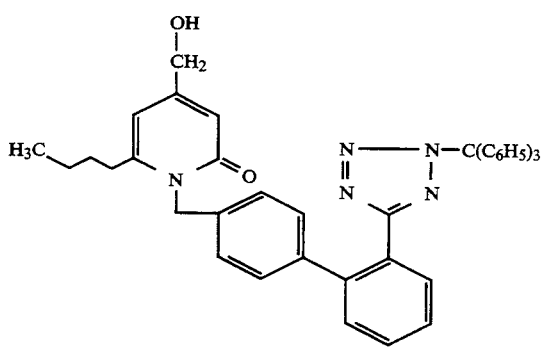

A 3.5 molar solution of sodium bis(2-methoxyethoxy)dihydroaluminate in toluene is diluted 1:10 with THF so that a 0.35 molar solution results. 43 ml (15 mmol) of this solution are added dropwise at 0° C. to a solution of 6.86 g (10 mmol) of the compound from Example I in 25 ml of THF, and the mixture is stirred for 1 hour at 0° C. and for 3 hours at room temperature. It is cooled again to 0° C., a further 14.3 ml (5 mmol) of the aluminate solution are added dropwise and the mixture is stirred overnight at room temperature.

Water is then cautiously added dropwise until the evolution of gas is complete, followed by 6N hydrochloric acid until a pH of about 7 is present. After addition of kieselguhr, the solid is filtered off with suction and the residue is boiled three times with 150 ml of THF/ethyl acetate (1:1) each time. The combined filtrates are extracted with water and satd. sodium chloride solution, and the organic phase is dried over Na$_2$SO$_4$ and concentrated in a rotary evaporator. The residue is chromatographed on 200 g of silica gel (230–400 mesh) using dichloromethane/ethyl acetate (10:1)→(1:2).

Yield: 3.82 g (58%) of colourless foam R$_f$: 0.37 (dichloromethane/methanol 10:1).

Example XXIX

6-Butyl-4-methoxymethyl-2-oxo-1{[2'-(N-triphenyl-methyl-tetrazol-5-yl)biphenyl-4-yl]methyl}-1,2-dihydropyridine

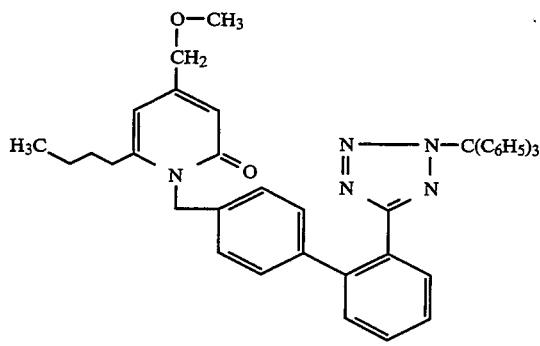

658 mg (1 mmol) of the compound from Example I are added dropwise at 0° C. under argon to a suspension of 31.5 mg (1.05 mmol) of 80% strength sodium hydride in 5 ml of THF. A solution of 142 mg (1 mmol) of methyl iodide in 2 ml of THF is then added dropwise and the mixture is stirred for 3 days at room temperature. It is treated with about 50 ml of water, extracted three times with 30 ml of ethyl acetate each time, and the combined organic phases are dried over $Na_2SO_4$ and concentrated to dryness. The residue is chromatographed on 18 g of silica gel (230–400 mesh) using dichloromethane→dichloromethane/ethyl acetate 1:2.

Yield: 371 mg (55%) of colourless foam $R_f$: 0.47 (dichloromethane/ethyl acetate 3:1).

Example XXX

4-Butyl-6-methyl-2-oxo-1-{[2'-(N-triphenylmethyl-tetrazol-5-yl)-biphenyl-4-yl]methyl}-1,2-dihydropyridine

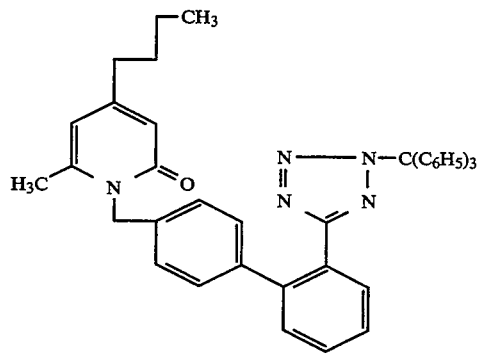

The title compound is obtained as a by-product in 3% yield during the chromatographic purification (silica gel, petroleum ether/ethyl acetate 1:1) of the compound from Example XXIV.

$R_f$: 0.42 (petroleum ether/ethyl acetate 1:1).

Example XXXI

6-Butyl-4-dimethylcarbamoyl-2-oxo-1{[2'-(N-triphenylmethyl-tetrazol-5-yl)-biphenyl-4-yl]methyl}-1,2-dihydropyridine

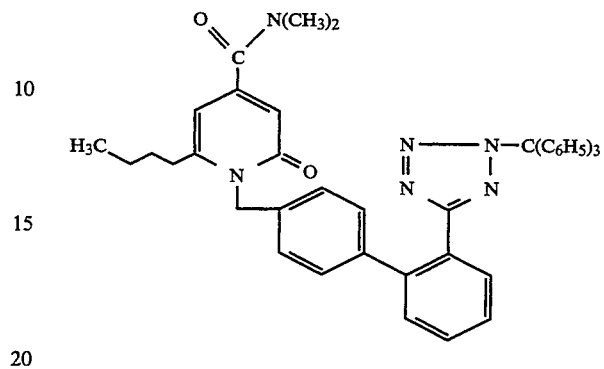

3 ml (6 mmol) (of a 2M solution of trimethylaluminium in toluene are diluted under argon with 5 ml of toluene. 0.44 ml (0.3 g, 6.6 mmol) of condensed dimethylamine are added dropwise to this mixture at −10° C. to −15° C., and it is stirred for 15 minutes at −15° C. and for 45 minutes at room temperature. A solution of 2 g (3 mmol) of the compound from Example I in 5 ml of toluene is then added dropwise and the mixture is boiled under reflux for 2 hours.

After cooling, it is treated cautiously with 50 ml of water and 7 ml of 1N hydrochloric acid, and the suspension is stirred vigorously for 15 minutes and extracted twice with ethyl acetate. The organic phases are washed with satd. sodium chloride solution, dried over $Na_2SO_4$ and concentrated. The residue is chromatographed on 50 g of silica gel (230–400 mesh) using dichloromethane/methanol 40:1→10:1.

Yield: 0.86 g (41%) of yellowish foam $R_f$: 0.7 (dichloromethane/methanol, 10:1).

Example XXXII

6-Butyl-4-methoxycarbonyl-2-oxo-1[(2'-tetrazol-5-yl-biphenyl-4-yl)methyl]-1,2-dihydropyridine

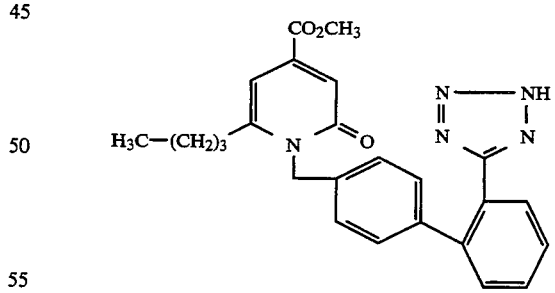

Process A

A solution of 3.0 g (4.37 mmol) of the compound from Example I in 40 ml of acetone is stirred for 30 min at RT with 0.4 ml of 37% strength hydrochloric acid and then heated on the water bath for about 1 min. After addition of a further 0.4 ml of 37% strength hydrochloric acid, the process is repeated.

The mixture is concentrated to dryness and the residue is chromatographed on 90 g of silica gel, 230–400 mesh, using dichloromethane, dichloromethane/methanol (50:1)→(10:1).

Yield: 1.045 g (54%) of colourless foam

Process B 5 g (7.3 mmol) of the compound from Example I are suspended in 35 ml of methanol and treated with 2.5 ml of conc. hydrochloric acid, by means of which a clear solution is formed.

The mixture is stirred for 3 hours at room temperature, and the deposited precipitate is filtered off, washed with methanol and dried in vacuo over $P_2O_5$.

Yield: 2.6 (80.3%) of colourless solid of m.p.209° C. (dec.). MS(FAB)=444 (100%, M+H), 235, (93%)

The compounds shown in Table II are prepared in analogy to the procedure of Example XXXII (process A or B).

TABLE II

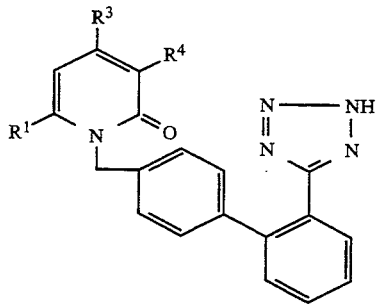

| Ex. No. | $R^1$ | $R^3$ | $R^4$ | Yield (% of theory)/process | MS (FAB/(DCI) | Starting material |
|---|---|---|---|---|---|---|
| XXXIII | -n-$C_4H_9$ | H | H | 27/A | 424 (50%, M + H) 386 (100%, M + H) | II |
| XXXIV | —$C_2H_5$ | —$C_2H_5$ | CN | 58/A | 386 (100%, M + H) | III |
| XXXV | -n-$C_4H_9$ | —$CO_2C_2H_5$ | H | 19/A | 411 (70%, M + H) 411 (70%, M + H) | IV |
| XXXVI | -n-$C_4H_9$ | —$CO_2CH(CH_3)_2$ | H | 67/B | 472 (100%, M + H) | V |
| XXXVII | -n-$C_3H_7$ | —$CO_2CH_3$ | H | 44/A | 430 (100%, M + H) | VI |
| XXXVIII | -n-$C_3H_7$ | —$CO_2C_2H_5$ | H | 51/A | 444 (100%, M + H) | VII |
| XXXIX | —$C_2H_5$ | —$CO_2CH_3$ | H | 67/A | 416 (100%, M + H) | VIII |
| XL | ◁ | —$CO_2CH_3$ | H | 70/A | 428 (100%, M + H) | IX |
| XLI | -n-$C_5H_{11}$ | —$CO_2CH_3$ | H | 71/B | 458 (100%, M + H) | X |
| XLII | —$CH_3$ | —$CO_2C_2H_5$ | H | 73/B | 460 (100%, M + H) | XI |
| XLIII | -n-$C_4H_9$ | —$CO_2CH_2$—$C_6H_5$ | H | 53/A | 520 (100%, M + H) | XII |
| XLIV | -n-$C_3H_7$ | H | H | 75/A | 372 (100%, M + H) | XIII |
| XLV | -n-$C_4H_9$ | —$CONH_2$ | H | 75/A | 429 (100%, M + H) | XIV |
| XLVI | -n-$C_4H_9$ | —CO—NH—$CH_2$—$C_6H_5$ | H | 65/A | 519 (100%, M + H) | XV |
| XLVII | -n-$C_4H_9$ | —$CO_2C_2H_5$ | —CN | 51/A | 483 (50%, M + H) 235 (100%, M + H) | XVI |
| XLVIII | -n-$C_3H_7$ | —$CO_2C_2H_5$ | —CN | 39/A | 469 (50%, M + H) 235 (100%, M + H) | XVII |
| XLIX | —$C_2H_5$ | —$CO_2C_2H_5$ | —CN | 38/A | | XVIII |
| L | ◁ | —$CO_2C_2H_5$ | —CN | 45/A | 467 (60%, M + H) 295 (100%) | XIX |
| LI | -n-$C_3H_7$ | H | —CN | 42/A | 397 (50%, M + H) 235 (100%) | XX |
| LII | -n-$C_4H_9$ | —$CH_3$ | —CN | 47/A | 425 | XII |

TABLE II-continued

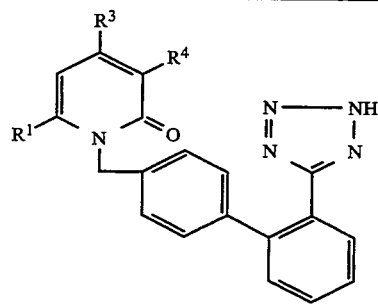

| Ex. No. | $R^1$ | $R^3$ | $R^4$ | Yield (% of theory)/process | MS (FAB/(DCI) | Starting material |
| --- | --- | --- | --- | --- | --- | --- |
| LIII | -n-$C_3H_7$ | -n-$C_3H_7$ | —CN | 52/A | (60%, M + H) 235 (100%) 439 | XI |
| LIV | -n-$C_4H_9$ | —$CH_2OH$ | H | 93/A | (90%, M + H) 235 (100%) 416 | XXVIII |
| LV | -n-$C_4H_9$ | —$CH_2OCH_3$ | H | 59/A | (100%, M + H) 430 | XXIX |
| LVI | -n-$C_3H_7$ | —CO—$NH_2$ | H | 67/A | (100%, M + H) 415 | XXVI |
| LVII | -n-$C_3H_7$ | —CONH—$CH_2$—$C_6H_5$ | H | 43/A | (100%, M + H) 505 | XXVII |
| LVIII | -n-$C_3H_7$ | —$CH_2$—O—CO—$C_6H_5$ | H | 60/A | (100%, M + H) 506 | XXV |
| LIX | -n-$C_4H_9$ | —$CH_3$ | H | 48/A | (70%), M + H) 400 | XXIV |
| LX | —$CH_3$ | -n-$C_4H_9$ | H | 46/A | (90%, M + H) 400 | XXX |
| LXI | -n-$C_3H_7$ | -n-$C_3H_7$ | H | 69/A | (70%, M + H) 414 | XXI |
| LXII | -n-$C_4H_9$ | —CO—$N(CH_3)_2$ | H | 74/B | (100%, M + H) 457 (100%, m + H) | XXXI |

Example LXIII

4-Hydroxymethyl-2-oxo-6-propyl-1[(2'-tetrazol-5-yl-biphenyl-4-yl)methyl]-1,2-dihydropyridine

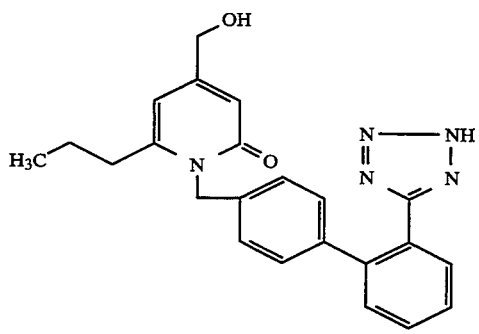

120 mg (0.24 mmol) of compound from Example LVIII are stirred at room temperature for 1 hour in 6 ml of methanol which contains 14 mg (0.26 mmol) of sodium methoxide. After addition of 0.28 ml of 1N hydrochloric acid, the mixture is concentrated and the residue is chromatographed on 10 g of silica gel using dichloromethane/methanol 20:1→5:1.

Yield: 92 mg (97%) of colourless foam FAB-MS:402(100%, M+H).

Example LXIV

6-Butyl-4-methylcarbamoyl-2-oxo-1[(2'-tetrazol-5-yl-biphenyl-4-yl)-methyl]1,2-dihydropyridine

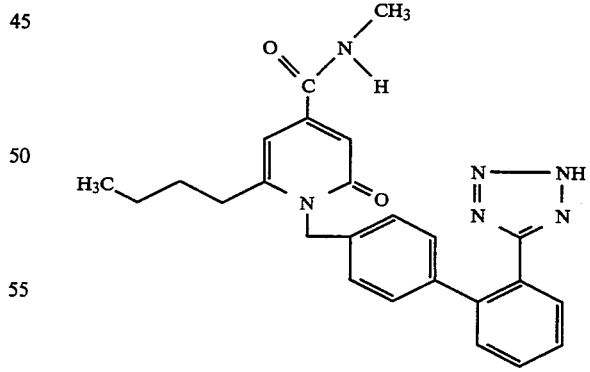

0.67 g (1.5 mmol) of the compound from Example XXXII are boiled under reflux for 10 minutes in 7.5 ml of THF, 2.5 ml of $CH_3OH$ and 5 ml of 40% strength aqueous methylamine solution. After concentration and filtration through 50 g of silica gel using dichloromethane/methanol (5:1), 0.56 g (84%) of amorphous colourless solid remains.

FAB-MS:443(80%, M+H).

Example LXV

6-Butyl-4-cyclopropylcarmaboyl-2-oxo-1-[(2'-tetrazol-5-yl-biphenyl-4-yl)-methyl]-1,2-dihydropyridine

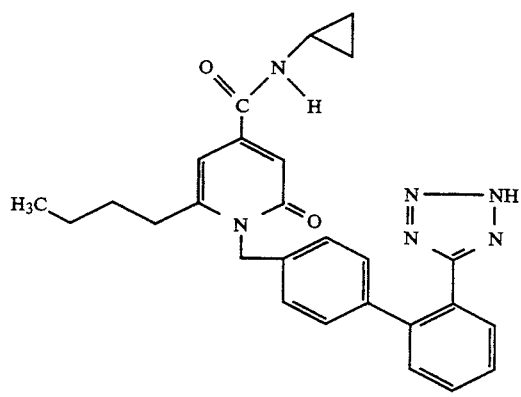

0.67 g (1.5 mmol) of the compound from Example XXXII are boiled under reflux for 4 hours in 10 ml of cyclopropylamine. After stripping off the amine, the residue is dissolved in 5 ml of THF and 5 ml of methanol, treated with 0.33 μl of conc. hydrochloric acid and concentrated again. The residue is chromatographed on 20 g of silica gel using dichloromethane/methanol (5:1).

Yield: 0.48 g (68%) of amorphous solid FAB-MS:469 (90%, M+H).

Example LXVI

6-Butyl-2-oxo-4-(2-phenylethyl-carbamoyl)-1-[(2'-tetrazol-5-yl-biphenyl-4-yl)-methyl]-1,2-dihydropyridine 2-phenylethyl-ammonium salt

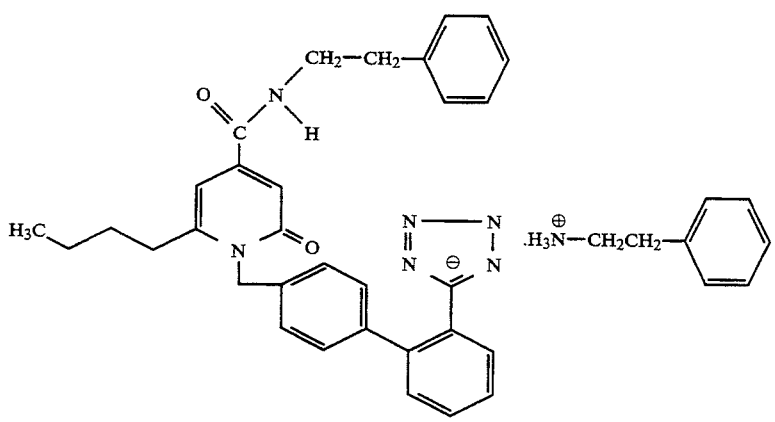

215 mg (0.5mmol) of the compound from Example LXX are dissolved in 10 ml of DMF with 181 mg (1.5 mmol) of 2-phenethylamine and 77 mg (0.5 mmol) of hydroxybenzotriazole and the mixture is treated at 0° C. with 106 mg (0.55 mmol) of N-(3-dimethylaminopropyl)-N-ethylcarbodiimide hydrochloride and stirred at room temperature for 1.5 hours. After addition of 50 ml of water, it is extracted three times with 30 ml of ethyl acetate each time, and the combined organic phases are dried over $Na_2SO_4$ and concentrated. Chromatography on 12 g of silica gel (230–400 mesh) using dichloromethane→dichloromethane/methanol 10:1 gives 80 mg (25%) of a colourless foam.

FAB-MS:654 (12%, M+H), 533 (100%, M-$C_8H_{11}N$+H).

Example LXVII

6-Ethyl-4-methoxycarbonyl-2-oxo-1-{[2'-(N-(1,1-dimethyl-3-oxo-butyl)-tetrazol-5-yl)-biphenyl-4-yl]-methyl}-1,2-dihydropyridine

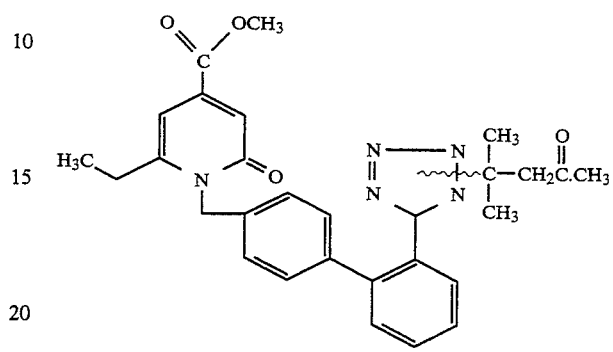

In a modification of the procedure from Example XXXII/A three times the amount of 37% strength hydrochloric acid is employed in the preparation of the compound from Example XXXIX. In this process, the title compound is obtained as a by-product in the chromatographic separation (colourless foam, yield: 25%).

$^1$H-NMR ($D_6$-DMSO): 1.53 (s,6H); 1.95 (s,3H); 3.15 (s,3H).

Example LXVIII

4-Dimethylcarbamoyl-6-ethyl-2-oxo-1-[(2'-tetrazol-5-yl-biphenyl-4-yl)-methyl]-1,2-dihydropyridine

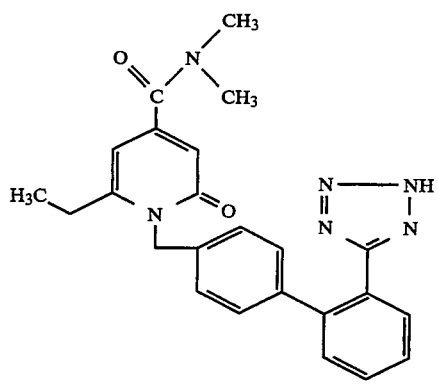

746 mg (1.45 mmol) of the compound from Example LXVII are heated to boiling for 5 minutes in 10 ml of methanol and 5 ml of 40% strength aqueous dimethylamine solution. After concentration, the residue is chromatographed on 40 g of silica gel using dichloromethane/methanol→5:1.

Yield: 73 mg (12%) of colourless foam FAB-MS: 429(58%, M+H), 154 (100%).

Example LXIX

6-Butyl-4-methoxymethyl-2-oxo-1-{[2'-(N-methyl)-tetrazol-5-yl)-biphenyl-4-yl]-methyl}-1,2-dihydropyridine

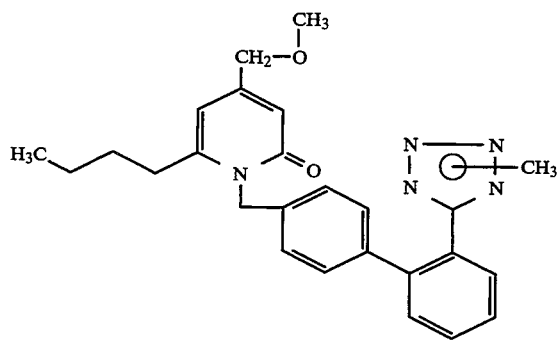

Analogously to the procedure from Example XXIX, in which the mixture is stirred for 2 hours at room temperature and 0.5 hours under reflux, 380 mg (84%) of a colourless foam are obtained from 435 mg (1 mmol) of the compound from Example LV. This is a 1:2 mixture of two N-methyl isomers.

FAB-MS: 444 (100%, M+H). $^1$H-NMR (CDCl$_3$): 3.23 (s,2H,N—CH$_3$); 3.42 (two s,3H,OCH$_3$); 4.23 (s,1H,N—CH$_3$); 4.3 (s,2H,CH$_2$—O).

Example LXX

6-Butyl-4-carboxy-2-oxo-1-[(2'-tetrazol-5-yl-biphenyl-4-yl)-methyl]-1,2-dihydropyridine

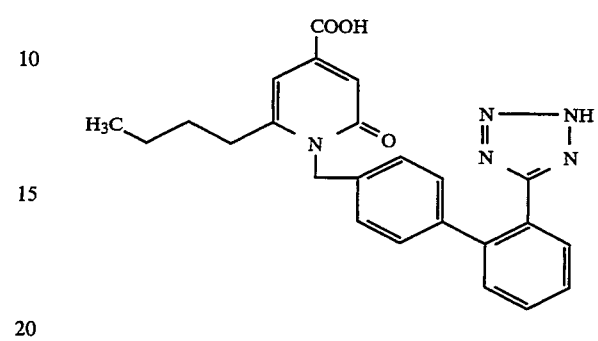

4.4 g (10 mmol) of the compound from Example XXXII are stirred at room temperature for 1.5 hours in 160 ml of methanol and 7 ml (35 mmol) of 5N sodium hydroxide solution. The mixture is then treated with 6.5 ml (39 mmol) of 6N hydrochloric acid and concentrated, and the residue is filtered through 200 g of silica gel using dichloromethane/methanol/acetic acid (10:1:0.3). From the eluate, an oily residue is obtained which is stirred with ether and filtered off with suction.

Yield: 3.8 g (88%) of colourless solid FAB-MS:430 (100%, M+H); 452 (30%, M+Na).

The compounds shown in Table III are prepared in analogy to the procedure of Example LXX.

TABLE III

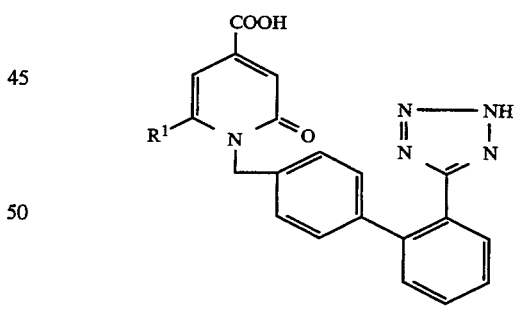

| Ex. No. | R$^1$ | Yield (% of theory) | MS |
|---|---|---|---|
| LXXI | -n-C$_3$H$_7$ | 84% | 416 (100%, M + H) |
| LXXII | —C$_2$H$_5$ | 92% | |
| LXXIII | ◁ | 71% | 414 (70%, M + H) |
| LXXIV | -n-C$_5$H$_{11}$ | 76% | 444 (70%, M + H) |

Example LXXV

6-Butyl-4-methoxycarbonyl-2-oxo-1[(2'-tetrazol-5-yl-biphenyl-4-yl)methyl]1,2-dihydropyridine potassium salt

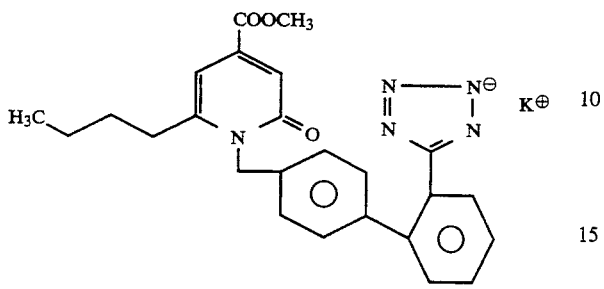

1.33 g (3 mmol) of the compound from Example XXXII are dissolved hot in 30 ml of THF and 30 ml of methanol, the solution is treated with 15 ml of water and 2.85 ml of 1N potassium hydroxide solution are added dropwise at about 5° C. The mixture is concentrated to dryness, and the residue is stirred in ether, filtered off and dried over $P_2O_5$ in vacuo.

Yield: 1.25 g (86.5%) of colourless amorphous solid FAB-MS: 482 (100%, M+H), 520 (20%, M+K). $^1$H-NMR, [$D_6$]-DMSO δ=0.8 [t,3H, $(CH_2)_3CH_3$] 3.35 [s,3H,COOCH$_3$] 5.3 [s,2H,N—CH$_2$]

Example LXXVI

6-Butyl-4-isopropyloxycarbonyl-2-oxo-1[(2'-tetrazol-5-yl-biphenyl-4-yl)-methyl]-1,2-dihydropyridine sodium salt

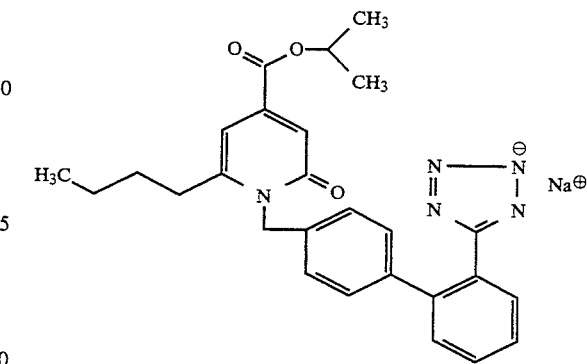

838 mg (1.78 mol) of the compound from Example XXXVI are dissolved in 5 ml of THF and 5 ml of water and the mixture is treated dropwise at about 5° C. with 1.69 ml of 1N sodium hydroxide solution. The THF is stripped off in vacuo and the mixture is then lyophilised.

Yield 600 mg (94%) of colourless foam FAB-MS: 516 (100% M+Na); 494 (70% M+H).

The compounds shown in Table IV are prepared in analogy to the procedures of Examples LXXV and LXXVI.

TABLE IV

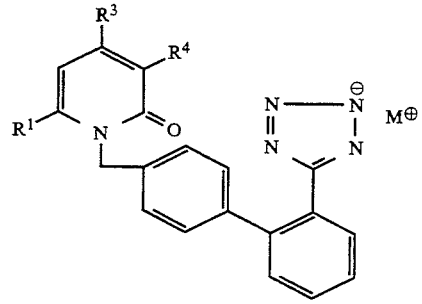

| Ex. No. | $R^1$ | $R^3$ | $R^4$ | M | Yield (% of theory) | MS | Analogously to Example No. |
|---|---|---|---|---|---|---|---|
| LXXVII | -n-$C_4H_9$ | —$CO_2C_2H_5$ | H | Na | 96 | 502 (100%) 480 (95%, M + H) | LXXVI |
| LXXVIII | -n-$C_3H_7$ | —$CO_2CH_3$ | H | Na | 88 | 452 (90%, M + H) | LXXVI |
| LXXIX | —$C_2H_5$ | —$CO_2CH_3$ | H | Na | 94 | | LXXVI |
| LXXX | ◁ | —$CO_2CH_3$ | H | Na | 92 | | LXXVI |
| LXXXI | -n-$C_3H_7$ | —$CO_2^{\ominus}Na^{\oplus}$ | H | Na* | 98 | 460 (80%, M + H) 482 (60%, M + Na) | LXXV |
| LXXXII | -n-$C_4H_9$ | —$CH_2$—$OCH_3$ | H | K | 92 | 468 (100%, M + H) | LXXVI |
| LXXXIII | -n-$C_4H_9$ | —$CH_2OH$ | H | K | 88 | 454 (10%, M + H) 307 (100%) | LXXVI |
| LXXXIV | —$C_2H_5$ | —$CO_2^{\ominus}Na^{\oplus}$ | H | Na*) | 98 | | LXXVI |
| LXXXV | -n-$C_4H_9$ | —$CONH_2$ | H | Na | 93 | | LXXVI |
| LXXXVI | -n-$C_4H_9$ | —$CONHCH_3$ | H | Na | 98 | 465 (70%, M + H) 491 (70%, M + H) | LXXVI |
| LXXXVII | -n-$C_4H_9$ | —CONH—◁ | H | Na | 97 | 469 (100%, M − Na + H) | LXXVI |
| LXXXVIII | -n-$C_4H_9$ | —$CH_3$ | H | Na | 98 | 422 (90%, M + H) 400 (100%, M − Na + H) | LXXVI |

TABLE IV-continued

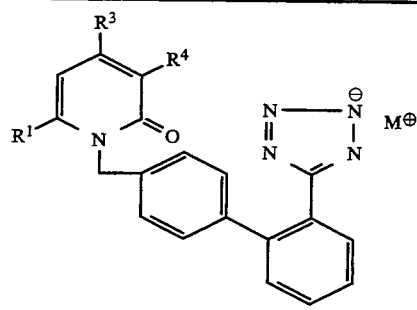

| Ex. No. | R¹ | R³ | R⁴ | M | Yield (% of theory) | MS | Analogously to Example No. |
|---|---|---|---|---|---|---|---|
| LXXXIX | ▷ | —$CO_2^\ominus Na^\oplus$ | H | Na*) | 98 | 458 (50%, M + H) 436 (60%, M − Na + H) | LXXVI |
| XC | -n-$C_3H_7$ | —$(CH_2)_2CH_3$ | H | Na | 94 | 436 (100%, M + H) | LXXVI |
| XCI | -n-$C_4H_9$ | —$CON(CH_3)_2$ | H | Na | 96 | 479 (100%, M + H) | LXXVI |

*)2 mol equivalents of sodium hydroxide solution are employed

Example XCII

6-Butyl-4-carboxy-2-oxo-1[(2'-tetrazol-5-yl-biphenyl-4-yl)methyl-1,2-dihydropyridine disodium salt

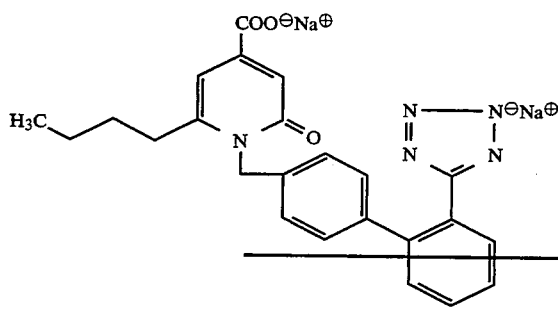

A suspension of 0.66 g (1.5 mmol) of the compound from Example XXXII is stirred at room temperature for 2 hours with 3 ml of 1N sodium hydroxide solution in 30 ml of THF and 15 ml of water, a clear solution resulting. It is concentrated to dryness, and the residue is stirred in THF/ether, filtered off with suction and dried in vacuo over $P_2O_5$.

Yield: 0.7 g (99%) m.p. from 290° C. (dec.) FAB-MS: 474 (70%, M+H); 452 (70% M—Na+H)

The compounds shown in Table V are prepared in analogy to the procedure of Example XCII. Compounds, which cannot be collected by filtration are lyophilised.

TABLE V

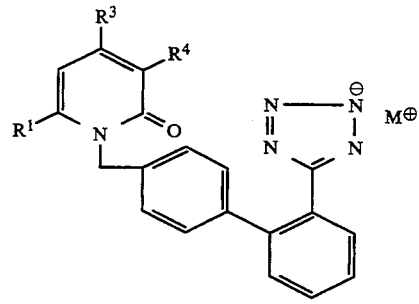

| Ex. No. | R¹ | R³ | R⁴ | M | Yield (% of theory) | MS | Starting materials/ Ex. No. |
|---|---|---|---|---|---|---|---|
| XCIII | -n-$C_2H_5$ | —$CO_2^\ominus Na^\oplus$ | CN | Na | 80 | | |
| XCIV | ▷ | —$CO_2^\ominus Na^\oplus$ | CN | Na | 36 | 483 (20%, M + H) 461 (100%, M − Na + H) | |
| XCV | -n-$C_3H_7$ | —$CO_2^\ominus Na^\oplus$ | CN | Na | 99 | 485 (60%, M + H) | |
| XCVI | -n-$C_4H_9$ | —$CO_2^\ominus Na^\oplus$ | CN | Na | 88 | 499 (70%, M + H) | |
| XCVII | $CH_3OCH_2$— | —$CO_2^\ominus K^\oplus$ | CN | K*) | 96 | 519 (50%, M + H) | CXLVII |
| XCVIII | -n-$C_5H_{11}$ | —$CO_2^\ominus Na^\oplus$ | H | Na | 99 | 488 (60%, M + H) | XLI |
| XCIX | $CH_3OCH_2$— | —$CO_2^\ominus Na^\oplus$ | H | Na | 100 | 462 (40%, M + H) | CXLIX |

*potassium hydroxide solution is employed instead of sodium hydroxide solution

The compounds shown in Table VI are prepared in analogy to the procedure of Example I/B, tert-butyl 4'-bromomethyl-triphenyl-2-carboxylate being employed as the alkylating agent:

TABLE VI

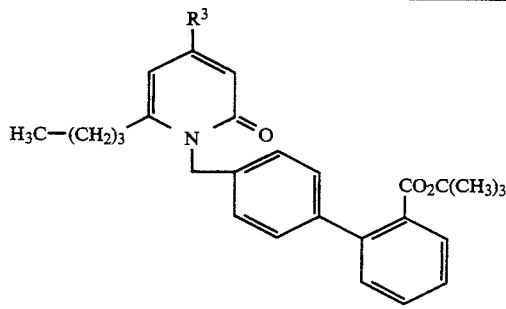

| Example No. | R³ |
|---|---|
| C | —CO₂CH₃ |
| CI | —CO₂—CH₂—C₆H₅ |

Example CII

6-Butyl-4-carboxy-2-oxo-1-[(2'-carboxy-biphenyl-4-yl)-methyl]-1,2-dihydropyridine

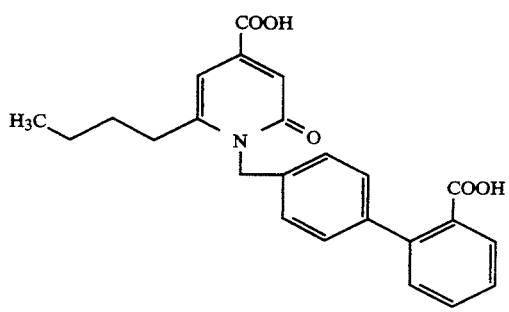

390 mg (0.71 mmol) of the compound from Example CI are reacted at 20° C. with 1 ml of trifluoroacetic acid in 4 ml of dichloromethane. After 3 hours, the mixture is treated with 2M aqueous sodium hydroxide solution and extracted with ether. Residues of organic solvent are removed in vacuo in a rotary evaporator, and the product is precipitated from the alkaline solution at 0° C. using 2M aqueous hydrochloric acid. The precipitate is filtered off with suction, washed with water and dried over phosphorus pentoxide and sodium hydroxide in a high vacuum.

Yield: 240 mg (68%) $R_f$=0.09 (dichloromethane:methanol=7:1).

Example CIII

6-Butyl-4-methoxycarbonyl-2-oxo-1-[(2'-carboxy-biphenyl-4-yl)-methyl]-1,2-dihydropyridine

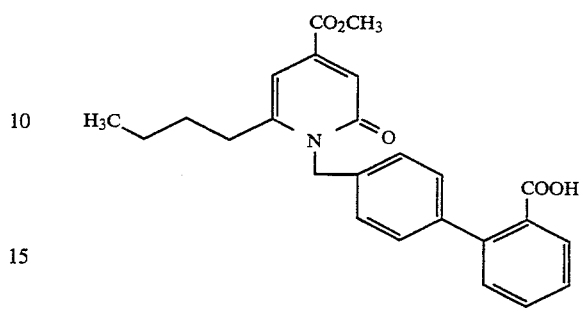

4.52 g (9.5 mmol) of the compound from Example C are reacted with 100 ml of 37% strength hydrochloric acid in 210 ml of dioxane. After 20 minutes at 20° C., the mixture is poured into water/ethyl acetate, and extracted several times with ethyl acetate, and the combined organic phases are dried using sodium sulphate and evaporated. After chromatographic purification on silica gel 60 (Merck, from dichloromethane via dichloromethane:methanol=100:1, 50:1, 20:1, 10:1, to methanol), 3.56 g (89% of theory) of product are obtained. $R_f$=0.19 (dichloromethane:methanol=20:1).

Example CIV

6-Butyl-4-methoxycarbonyl-2-oxo-1-{[2-(4-tolyl-sulphonylcarbamoyl)-biphenyl-4-yl]methyl}-1,2-dihydropyridine

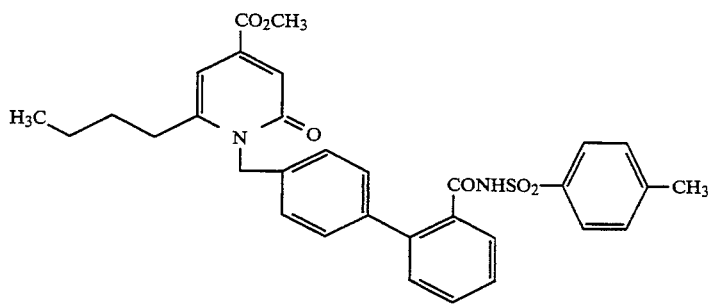

1.063 g (2.53 mmol) of the compound from Example C are reacted at 0° C. with 0.22 ml (2.78 mmol) of methanesulphonyl chloride and 0.512 g (5.06 mmol) of triethylamine in 10 ml of tetrahydrofuran with exclusion of water. After 30 minutes, 0.52 g (3.04 mmol) of 4-toluenesulphonamide and 0.31 g (2.53 mmol) of 4-(N,N-dimethylamino)pyridine are added and the mixture is stirred for 20 hours with warming to 20° C. It is extracted with buffer (pH=2) and ethyl acetate, and the organic phase is dried using sodium sulphate and evaporated. Chromatographic purification (silica gel 60, Merck, dichloromethane-dichloromethane:methanol=100:1 to 50:1) yields 0.83 g (1 mmol) of product.

$R_f$=0.50 (dichloromethane:methanol=10:1).

Example CV

6-Butyl-4-methoxymethyl-2-oxo-1-{[(2'-methylsulphonylcarbamoyl-biphenyl-4-yl]methyl}-1,2-dihydropyridine

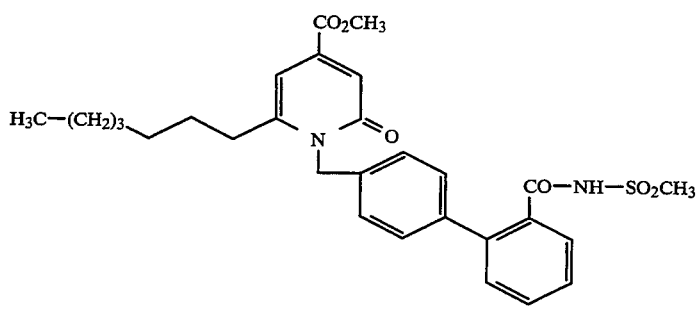

The title compound is prepared in analogy to the procedure of Example CIV, methanesulphonamide being used.

$R_f$=0.46 (dichloromethane:methanol=10:1).

The compounds shown in Table VII are prepared in analogy to the procedure of Example LXX.

TABLE VII

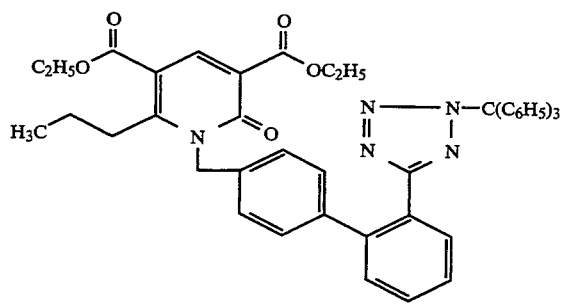

| Ex. | R[18] | Yield: (% of theory) | $R_f$ Dichloromethane: MeOH (5:1) | Starting material (Ex. No.) |
|---|---|---|---|---|
| CVI | —⌬—CH₃ | 95 | 0.17 | CIV |
| CVII | CH₃ | 71 | 0.04 | CV |

Example CVIII

6-Propyl-3,5-diethoxycarbonyl-2-oxo-1-{[2'-(N-triphenylmethyl-tetrazol-5-yl)-biphenyl-4-yl]methyl}-1,2-dihydropyridine

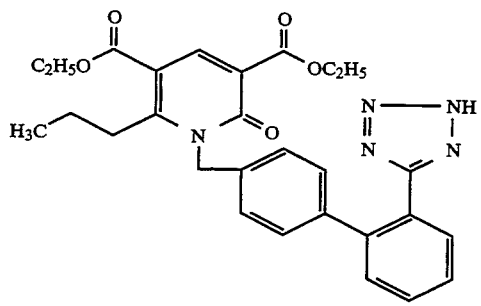

7.2 g (25.6mmol) of the compound from Example 23, 0.92 g (30.7 mmol) of sodium hydride (80% in oil) and 14.3 g (25.6 mmol) of N-triphenylmethyl-5-[2-(4'-bromomethylbiphenyl)]tetrazole are stirred at 20° C. overnight in 100 ml of dimethylformamide. The solvent is removed by distillation in vacuo, the residue is dissolved in ethyl acetate, and the solution is washed with water, dried over sodium sulphate and chromatographed on silica gel using petroleum ether/ethyl acetate 10:1.

Yield: 4.9 g (25% of theory). $R_f$: 0.17 petroleum ether/ethyl acetate 10:1.

Example CIX

6-Propyl-3,5-bis-ethoxycarbonyl-2-oxo-1[(2'-tetrazol-5-yl-biphenyl-4-yl)-methyl]-1,2-dihydropyridine

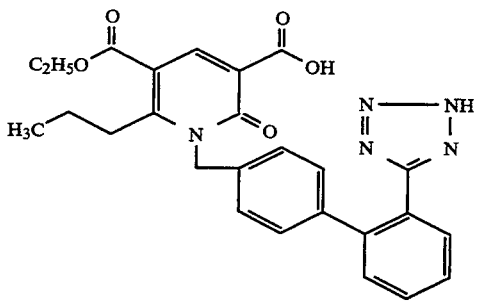

Analogously to Example XXXII, 1.1 g of the title compound are obtained from 1.9 g (2.5 mmol) of the compound from Example CVIII.

Yield: 85% of theory MS(FAB): 516 (M+1).

Example CX

6-Propyl-3-hydroxycarbonyl-5-ethoxycarbonyl-2-oxo-1-[2'-tetrazol-5-yl-biphenyl-4-yl)methyl]-1,2-dihydropyridine 2.0 g (2.6 mmol) of the compound Example CVIII and 145.6 mg (2.6 mmol) of potassium hydroxide are heated under reflux for 20 minutes in 27 ml of ethanol. The solvent is removed by distillation, and the residue is dissolved in water with addition of 1 g of potassium carbonate. The solution is washed with ethyl acetate, the aqueous phase is acidified with hydrochloric acid and the precipitated product is recrystallised from methylene chloride.

Yield: 0.1 g, 5.3% of theory Melting point: 128° C. (dec.).

Example CXI

6-Propyl-2-oxo-1-[(2'-tetrazol-5-yl-biphenyl-4-yl)-methyl]-1,2-dihydropyridine-3,5-dicarboxylic acid

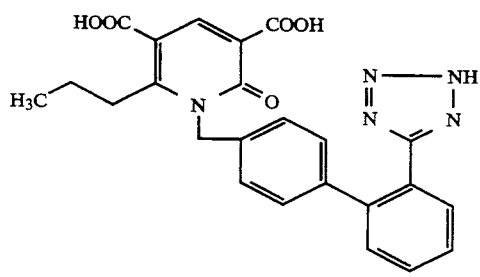

1.88 g (2.5 mmol) of Example CVIII and 1.12 g (20 mmol) of potassium hydroxide are heated under reflux for 48 hours in 50 ml of ethanol. The solvent is removed by distillation, the residue is dissolved in water, the solution is washed with ether, and the aqueous phase is acidified with hydrochloric acid and extracted with ethyl acetate. The organic phase is dried over sodium sulphate, the solvent is removed by distillation and the residue is triturated with ether.

Yield: 0.6 g, 48% of theory SI-MS: 458, (M−H)−

Examples CXII and CXIII

6-Propyl-3-hydroxymethyl-5-ethoxycarbonyl-2-oxo-1-{[2'-(N-triphenylmethyl-tetrazol-5-yl)-biphenyl-4-yl]methyl}-1,2-dihydropyridine (Example CXII)

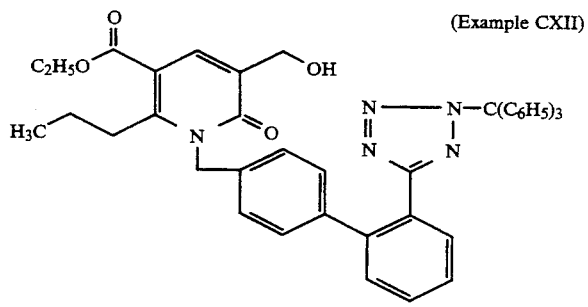

6-propyl-3,5-bis(hydroxymethyl)-2-oxo-1-{[2'-(N-triphenylmethyl-tetrazol-5-yl)-biphenyl-4-yl]methyl}-1,2-dihydropyridine (Example CXIII)

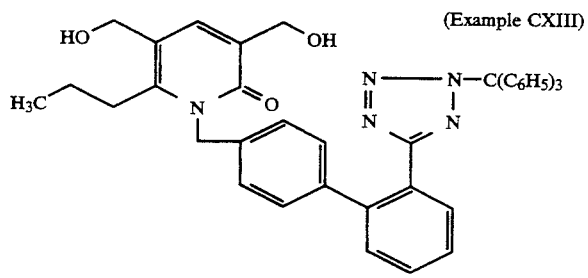

0.75 g (0.99 mmol) of the compound from Example CVIII and 0.58 ml (1.98 mmol) of Red-Al (3.4M in toluene) are stirred at 20° C. for 2 hours in 5 ml of THF. The mixture is hydrolysed with 25% strength potassium sodium tartrate solution and washed with ethyl acetate, and the organic phase is washed with saturated sodium chloride solution, dried over sodium sulphate and chromatographed on silica gel using ethyl acetate/petroleum ether (1:5).

Yield: 94 mg, 13.5% of theory (Example CXII)

Furthermore, 204 mg (29% of theory) of Example CXIII are obtained:

$R_f$ 0.35 ethyl acetate/petroleum ether (1:1) (Example CXII) $R_f$ 0.66 ethyl acetate (Example CXIII).

Example CXIV

6-Propyl-3-hydroxymethyl-5-ethoxycarbonyl-2-oxo-1[2'-tetrazol-5-yl-biphenyl-4-yl)methyl]1,2-dihydropyridine

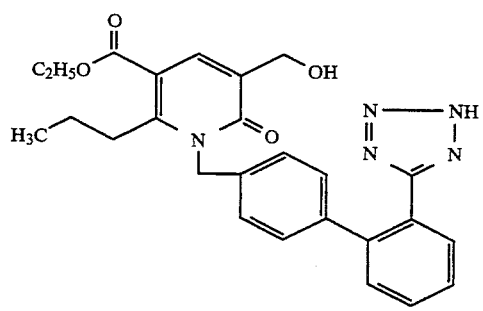

Analogously to Example XXXII, 37.6 mg of the title compound are obtained from 85 mg (0.121 mmol) of the compound from Example CXII.

Yield: 66% MS (FAB): 474 (M+1), 496 (M+Na).

Example CXV

6-Propyl-3,5-bis(hydroxymethyl)-2-oxo-1-[(2'-tetrazol-5-yl-biphenyl-4-yl)-methyl]-1,2-dihydropyridine

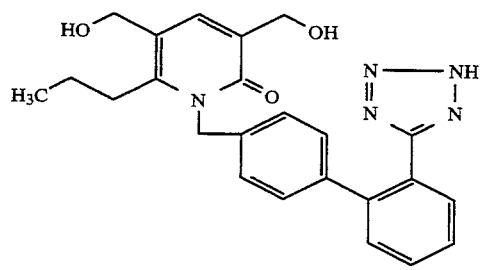

Analogously to Example XXXII, 85 mg of the title compound are obtained from 200 mg of the compound from Example CXIII.

Yield: 66.3% of theory MS (FAB):432 (M+H), 454 (M+Na). The compounds shown in Table VIII are prepared in analogy to the preparation procedures given there.

TABLE VIII

[Structure shown: a core compound with N—N—C(C₆H₅)₃ tetrazole group attached to a methylphenyl ring, labeled 25]

| Ex. No. | $R^1$ | $R^2$ | $R^3$ | $R^4$ | Yield (% of theory) | $R_f^*$ | Starting material/ process in analogy to Ex. No. |
|---|---|---|---|---|---|---|---|
| CXVI | n-C₃H₇ | —COOCH₂CH₃ | C₆H₅ | COOCH₃ | 46 | 0.21[1] | 25/CVIII |
| CXVII | n-C₃H₇ | —COOCH₂CH₃ | C₆H₅ | H | 18 | 0.2[2] | 27/CVIII |
| CXVIII | n-C₄H₉ | H | —COOCH₂CH₃ | COOCH₂CH₃ | 11 | 0.16[3] | 28/IB |
| CXIX | n-C₄H₉ | I | —COOCH₃ | I | 13 | 0.31[4] | 30/IB |
| CXX | —CH₂—CH₂—CH₂— | | —COOCH₂CH₃ | H | 65 | 0.16[1] | |
| CXXI | n-C₄H₉ | H | —COOCH₃ | —CH=CH—C₆H₅ | | | 31/IB |
| CXXII | CH₃OCH₂— | H | —COOCH₃ | CN | $R_f^*$ 25 | 0.25[4] | 32/IB |
| CXXIII | (CH₃)₂CH— | H | —COOCH₂CH₃ | CN | 5 | 0.22[1] | 33/IB |
| CXXIV | CH₃OCH₂— | H | —COOCH₃ | H | 46 | 0.11[2] | 34/IB |
| CXXV | (CH₃)₂CH— | H | —COOCH₃ | H | 12 | 0.20[2] | 35/IB |
| CXXVI | n-C₃H₇ | —COOCH₂CH₃ | H | H | 15 | 0.42[3] | 37/IB |
| CXXVII | n-C₃H₇ | —CH₂OH | H | H | 79 | 0.5[6] | CXXVI/XXVIII |
| CXXVIII | n-C₃H₇ | —CH₂OCH₃ | H | H | 96 | 0.25[3] | CXXVII/XXIX |
| CXXIX | -n-C₃H₇ | —CH₂OCH₂C₆H₅ | H | H | 85 | 0.39[3] | CXXVII/XXIX |
| CXXX | n-C₃H₇ | —CHO | H | H | 75 | 0.5[1] | CXXVII/pyridinium chlorochromate dichloromethane, RT |
| CXXXI | n-C₄H₉ | H | H | —COOCH₃ | 14 | 0.43[3] | 39/IB |
| CXXXII | n-C₄H₉ | H | —COOCH₂CH₃ | —COOH | 39 | 0.17[5] | CXVIII/VX |
| CXXXIII | n-C₄H₉ | H | —CH₂OH | —CH₂OH | 20 | 0.35[6] | CXVIII/XXVII |
| CXXXIV | Cl | H | H | H | 15 | 0.18[1] | 6-Chloro-pyrid-2-one/IB |

Solvent mixtures
*[1] Petroleum ether/ethyl acetate (2:1)
[2] Petroleum ether/ethyl acetate (10:1)
[3] Petroleum ether/ethyl acetate (5:1)
[4] Hexane/ethyl acetate (3:1)
[5] Dichloromethane/methanol (10:1)
[6] Petroleum ether/ethyl acetate (1:1)

Example CXXXV

Diethyl 6-butyl-1-[(2'-tetrazol-5-yl-biphenyl-4-yl)-methyl]-pyrid-2-one-3,4-dicarboxylate

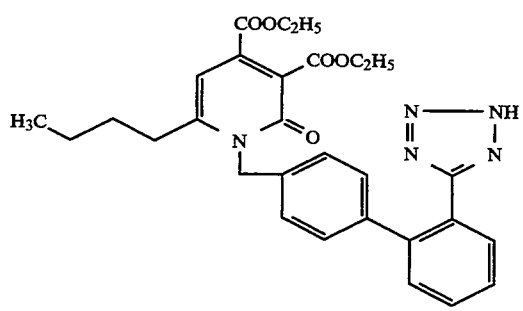

Analogously to Example XXXII, 0.35 g (51%) of the title compound is obtained from 1 g of the compound from Example CXVIII. MS(FAB) :530 (M+H), 552 (M+Na).

Example CXXXVI

6-Butyl-1-[(2'-tetrazol-5-yl-biphenyl-4-yl)-methyl]-pyrid-2-one-3,4-dicarboxylic acid

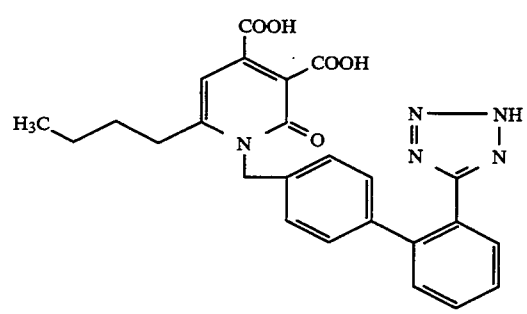

Analogously to the procedure for Example CXI, 120 mg of the title compound are obtained from 120 mg (0.28 mmol) of the compound from Example CXXXV.

Yield: 88% of theory $R_f$=0.16 (acetonitrilel/water 10:1).

The compounds of Table IX—if not stated otherwise, are prepared analogously to the process of XXXIIB.

The compounds shown in Table X are prepared by dissolving the appropriate acids or tetrazoles in methanol/THF and adding 1 eq. of potassium hydroxide, sodium hydroxide or lithium hydroxide, ½ eq. of caesium carbonate, ½ eq. of calcium oxide, sodium hydrogen carbonate or potassium hydrogen carbonate in water per acid group. The solvent is removed by distillation and the aqueous solution which remains is lyophilised.

TABLE IX

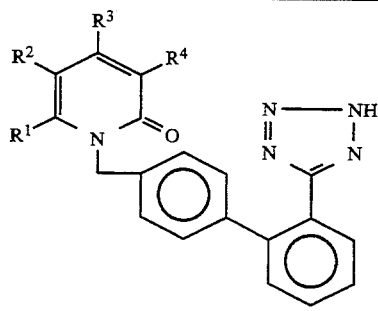

| Ex. No. | $R^1$ | $R^2$ | $R^3$ | $R^4$ | Yield (% of theory) | MS ($R_f$) | Starting material Ex. No. |
|---|---|---|---|---|---|---|---|
| CXXVII | -nC$_3$H$_7$ | —COOCH$_2$CH$_3$ | H | —COOCH$_2$CH$_3$ | 85 | 516 (M + H) | CVIII |
| CXXXVIII | n-C$_3$H$_7$ | CH$_2$OCH$_3$ | H | CH$_2$OCH$_3$ | | | CXIII |
| CXXXIX | n-C$_4$H$_9$ | H | H | CN | | | 6-Butyl-3-cyano-pyrid-2-on |
| CXL | -n-C$_3$H$_7$ | —COOCH$_2$CH$_3$ | —C$_6$H$_5$ | —COOCH$_3$ | 28 | ($R_f$ 0.37[1]) | CXVI |
| CXLI | -n-C$_3$H$_7$ | —COOCH$_2$CH$_3$ | —C$_6$H$_5$ | H | 77 | ($R_f$ 0.31[1]) | CXVII |
| CXLII | -n-C$_4$H$_9$ | I | —COOCH$_3$ | —I | 28 | ($R_f$ 0.43[2]) | CXIX |
| CXLIII | -n-C$_4$H$_9$ | H | —COOH | —I | | 556/80%, (M + H) 391/200%) | |
| CXLIV | -n-C$_4$H$_9$ | H | —COOCH$_3$ | (styryl) | | 652 (M + Ag) | CXXI |
| CXLV | —CH$_2$CH$_2$CH$_2$— | | —COOCH$_2$CH$_3$ | H | 89 | 441 (60%, M+) | CXX |
| CXLVI | —CH$_3$OCH$_2$— | H | —COOCH$_3$ | CN | 52 | 457 (60%, M + H) | CXXII |
| CXLVII | (CH$_3$)$_2$CH— | H— | —COOCH$_3$ | CN | 40 | 469 (80%, M + H) | CXXIII |
| CXLVIII | CH$_3$OCH$_2$— | H | —COOCH$_3$ | H | 89 | 431 (10%, M+) | CXXIV |
| CXLIX | (CH$_3$)$_2$CH— | H | —COOCH$_3$ | H | 79 | 429 (20%, M+) | CXXV |
| CL | n-C$_3$H$_7$ | CH$_2$OH | H | H | 76 | (0.19[1]) | CXXVI |
| CLI | n-C$_3$H$_7$ | CH$_2$OCH$_3$ | H | H | | | CXXVII |
| CLII | n-C$_3$H$_7$ | —CH$_2$OCH$_2$C$_6$H$_5$ | H | H | | | CXXVIII |
| CLIII | n-C$_3$H$_7$ | —COOCH$_2$CH$_3$ | H | H | 32 | (0.33[1]) | CXXIX |
| CLIV | -n-C$_3$H$_7$ | —COOH | H | H | | (0.13[1]) | Process from Ex. CX |
| CLV | -n-C$_3$H$_7$ | —CHO | H | H | | (0.1[3]) | CXXX |
| CLVI | n-C$_4$H$_9$ | H | H | —COOCH$_3$ | | | CXXXI |
| CLVII | -n-C$_4$H$_9$ | H | H | —COOH | | | CLVIII/process from Ex. CX |
| CLVIII | -n-C$_4$H$_9$ | H | —CO$_2$C$_2$H$_5$ | —COOH | 58 | (0.19[1]) | CXXXII |
| CLIX | -n-C$_4$H$_9$ | H | —CH$_2$OH | —CH$_2$OH | 62 | (0.28[4]) | CXXXIII/process from Ex. XXVIII |
| CLX | Cl | H | H | H | 71 | (0.29[1]) | CXXXIV |

[1] dichloromethane/methanol (10:1)
[2] dichloromethane/ethyl acetate (20:1)
[3] petroleum ether/ethyl acetate (2:1)
[4] dichloromethane/methanol (5:1)

TABLE X

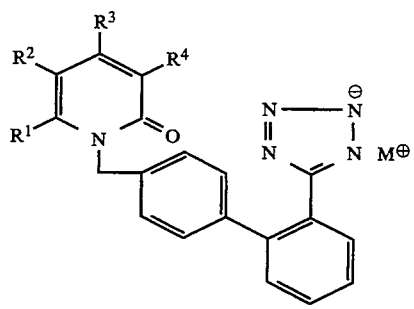

| Ex. No. | R¹ | R² | R³ | R⁴ | M⁺ | Yield (% of theory) | MS (R$_f$) | Starting material Ex. No. |
|---|---|---|---|---|---|---|---|---|
| CLXI | $CH_3-(CH_2)_2-$ | $-CO_2C_2H_5$ | H | $-CO_2C_2H_5$ | K | | | |
| CLXII | $CH_3-(CH_2)_2-$ | $-CO_2^{\ominus}K^{\oplus}$ | H | $-CO_2^{\ominus}K^{\oplus}$ | K | | | |
| CLXIII | $CH_3-(CH_2)_2-$ | $-CO_2C_2H_5$ | H | $-CO_2^{\ominus}K^{\oplus}$ | K | | | |
| CLXIV | $CH_3-(CH_2)_2-$ | $-CO_2C_2H_5$ | H | $-CH_2OH$ | K | | | |
| CLXV | $H_3C-(CH_2)_2-$ | $HO-CH_2$ | H | $-CH_2OH$ | K | | | |
| CLXVI | $H_3C-(CH_2)_2-$ | $-CO_2C_2H_5$ | $C_6H_5$ | $CO_2CH_3$ | K | | | |
| CLXVII | $H_3C-(CH_2)_2-$ | $-CO_2C_2H_5$ | $C_6H_5$ | H | K | | | |
| CLXVIII | $H_3C-(CH_2)_3-$ | H | $-CO_2C_2H_5$ | $-CO_2C_2H_5$ | K | | | |
| CLXIX | $H_3C-(CH_2)_3-$ | H | $-CO_2^{\ominus}K^{\oplus}$ | $-CO_2^{\ominus}K^{\oplus}$ | K | | | |
| CLXX | $H_3C-(CH_2)_3-$ | $-CO_2C_2H_5$ | H | H | K | | | |
| CLXXI | $H_3C-(CH_2)_3-$ | $-CO_2^{\ominus}K^{\oplus}$ | H | H | K | | | |
| CLXXII | $-CH_2CH_2CH_2-$ | | $-CO_2CH_2CH_3$ | H | Na | 95 | 464 (60%, M + H) | CXLVI |
| CLXXIII | $H_3C-(CH_2)_3-$ | H | $-CO_2CH_3$ | H | Li | 98 | 450 (80%, M + H) 456 (100%, M + Li) | XXXII |
| CLXXIV | $H_3C-(CH_2)_3-$ | H | $-CO_2CH_3$ | H | Cs | 97 | 708 (100% M + Cs) | XXXII |
| CLXXV | $H_3C-(CH_2)_4-$ | H | $-CO_2CH_3$ | H | Na | 94 | 480 (70%, M + H) | XLI |
| CLXXVI | $CH_3OCH_2$ | H | $-CO_2CH_3$ | H | Na | 100 | 454 (100%, M + H) | CXLIX |
| CLXXVII | $-n-C_4H_9$ | H | $-CO_2CH_3$ | H | ½ Ca | 95 | 482 (40%, M + ½ Ca) 925 (30%, 2M + H) | XXXII |
| CLXXVIII | $(CH_3)_2CH$ | H | $-CO_2CH_3$ | H | Na | 97 | 452 (100%, M + H) | CLXII |

Example CLXXIX

6-Butyl-4-methoxycarbonyl-2-oxo-1-[(2'-tetrazol-5-yl-biphenyl-4-yl)methyl]1,2-dihydropyridine sodium salt

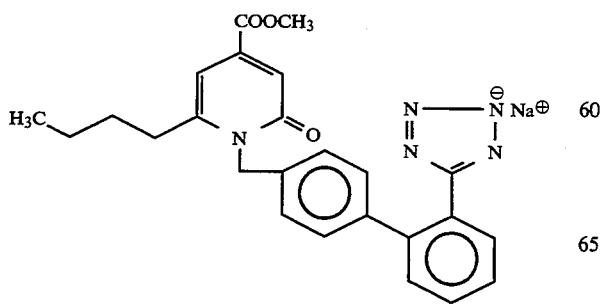

51 mg (0.95 mmol) of sodium methoxide are added to a solution of 443 mg (1 mmol) of the compound from Example XXXII in 10 ml of methanol and 5 ml of acetone, and the mixture is concentrated and lyophilised.

Yield: 460 mg (99% of theory) of amorphous solid

The compounds shown in Table XI are prepared by the procedure given there:

TABLE XI

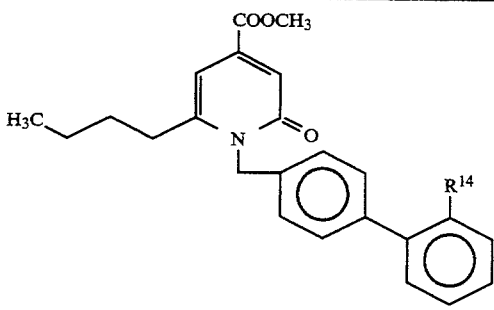

| Ex. No. | R[14] | Yield (% of theory) | R_f Petroleum ether/ethyl acetate (1:1) | 1H-NMR (D6DMSO) (tetrazole-CH3) |
|---|---|---|---|---|
| CLXXX | (N=N, N—N, CH3) | 40 | 0.25 | 4.28 ppm |
| CLXXXI | (N—N, N—N, CH3) | 44 | 0.15 | 3.45 ppm |

1.19 g (2.47 mmol) of the compound from Example LXXV are stirred at RT for 3 days with 770 mg (5.4 mmol) of methyl iodide in 30 ml of THF. The mixture is treated with 100 ml of water and extracted three times with 50 ml of dichloromethane each time, and the organic phase is dried, concentrated and chromatographed on 75 g of silica gel using petroleum ether-/ethyl acetate (2:1→1:3). 448 mg (40%) of Example CLXXVIII and 493 mg (44%) of Example CLXXXVII, are obtained, in each case as a colourless amorphous solid.

Starting from the compound of example CLXIII the following compounds are prepared:

TABLE XII

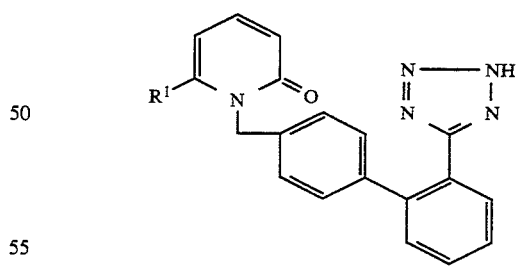

| Ex. No. | R | R_f* | Yield | reaction conditions |
|---|---|---|---|---|
| CLXXXII | CH3CH2O— | 0.29 | 86% | 05. NaOEt in EtOH, 1d. reflux |
| CLXXXIII | CH3CH2—S— | 0.29 | 24% | 0.16 MKSEt in THF 1d. reflux |
| CLXXXIV | CH3CH2—N—H | | | ges. H2NEt-Lsg. in TMF, 1d. reflux | solvent: dichloromethane/methanol (10:1)

The following compounds are obtained according to process B of example I

TABLE XIII

| Ex. No. | $R^1$ | $R^2$ | $R^3$ | $R^4$ | Yield (% of theory) | $R_f$* | Starting material Ex. No. |
|---|---|---|---|---|---|---|---|
| CLXXXV | n-C$_4$H$_9$ | H | CN | H | 28 | 0.43[1] | 40 |
| CLXXXVI | n-C$_4$H$_9$ | H | (N=N, N—N—C(C$_6$H$_5$)$_3$ tetrazole) | H | 12 | 0.7[2] | 42 |
| CLXXXVII | CH$_3$ | H | COOCH$_3$ | H | 33 | 0.27[2] | 6-methyl-4-methoxy-carbonyl-2-oxo-1,2,di-hydropyridine |
| CLXXXVIII | —(CH$_2$)$_4$— | | COOCH$_3$ | H | 43 | 0.33[2] | 4-methoxy-carbonyl-2-oxo-1,2,5,6,7,8 hexahydro-chinoline |

*solvent mixtures
[1] petrolether/ethylacetate 2:1
[2] petrolether/ethylacetate 1:1

The following compounds are synthesized according to the process given in table XIV

TABLE XIV

| Ex. No. | $R^1$ | $R^2$ | $R^3$ | $R^4$ | $M^\oplus$ | Yield (% of theory) | MS | Starting material Ex. No. | Process (according to Ex. No.) |
|---|---|---|---|---|---|---|---|---|---|
| CLXXXIX | n-C$_4$H$_9$ | H | CN | H | H | 48 | 410 (40%, M$^+$) | CLXXXV | XXXIIB |
| CXC | n-C$_4$H$_9$ | H | (N=N, N—NH tetrazole) | H | H | 68 | 454 (80%, M + H) | CLXXXVI | XXXIIB[1] |
| CXCI | CH$_3$ | H | COOCH$_3$ | H | H | 64 | 402 (100%, M + H) | CLXXXVII | XXXIIB |
| CXCII | —(CH$_2$)$_4$— | | COOCH$_3$ | H | H | 73 | 442 (100%, M + H) | CLXXXVIII | XXXIIB |
| CXCIII | CH$_3$ | H | COOH | H | H | 96 | 388 (80%, M + H) | CLXXXVIII | LXX |
| CXCIV | —(CH$_2$)$_3$— | | COO$^\ominus$H$^\oplus$ | H | H | 100 | 426 (40%, M + H) | CLXXXVIII | XCII |
| CXCV | CH$_3$—O—CH$_2$ | H | COOH | H | H | 40 | 418 (80%, M + H) | XCIX | Base: LiOH neutralization |

TABLE XIV-continued

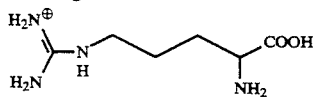

| Ex. No. | R¹ | R² | R³ | R⁴ | M⊕ | Yield (% of theory) | MS | Starting material Ex. No. | Process (according to Ex. No.) |
|---|---|---|---|---|---|---|---|---|---|
| CXCVI | $(CH_3)_2CH$ | H | $COO^-Na^+$ | H | Na | 99 | 460 (60%, M + H) | CXLIX | XCII with AeOH chromatography |
| CXCVII | $(CH_3)_2CH$ | H | COOH | H | H | 62 | 416 (100%, M + H) | CXCVI | neturalization with AeOH chromatography |
| CXCVIII | $n-C_4H_9$ | H | $COOCH_3$ | H | H—Arg[2] | 99 | 618 (80%, M + H) | XXXII | LXXVI Base: Argimine |
| CXCIX | $n-C_4H_9$ | H | $COOCH_3$ | H | $HNEt_3$ | 96 | 545 (50%, M + H) | XXXII | LXXVI Base: Triethylamine |
| CIC | $n-C_4H_9$ | H | $COOCH_3$ | H | $H_2NEt_2$ | 96 | 517 (40% M + H) | XXXII | LXXVI Base: Diethylamine |
| CC | $CH_3$ | H | $COOCH_3$ | H | Na | 100 | 424 (70%, M + H) | CXCVII | LXXVI Base: $NaHCO_3$ |

[1] double amount of conc. HCl was used
[2] H—Arg:

According to the process of example XCII the following compounds are synthesized, but it is stirred with one molar equivalent of NaOH overnight and lyophilized.

TABLE XV

| Ex. No. | R¹⁴ | Yield % of theory | MS | starting material |
|---|---|---|---|---|
| CCI | N=N, N—N—CH₃ (ring) | 97% | 466 (70%, M + H) | CLXXX |

TABLE XV-continued

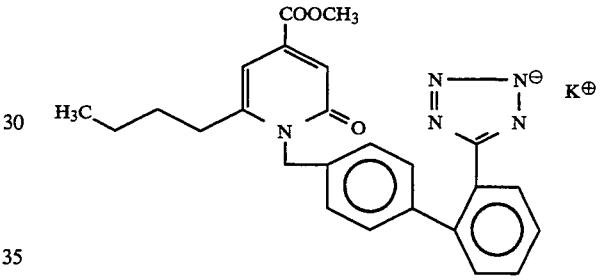

| Ex. No. | R[14] | Yield % of theory | MS | starting material |
|---|---|---|---|---|
| CCII | (structure shown) | 99% | 466 (100%, M + H) | CLXXXI |

We claim:
1. A compound of the formula

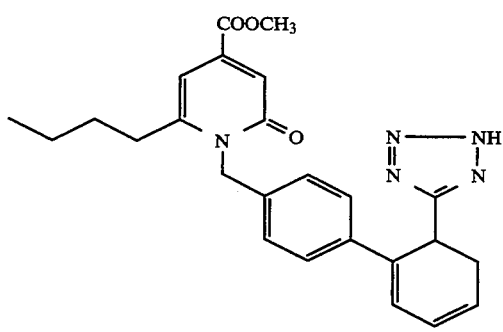

or a salt thereof.

2. The compound according to claim 1, wherein such compound is

3. A composition for the treatment of arterial hypertension comprising an amount effective therefore of a compound or salt thereof according to claim 1 and a pharmacologically acceptable diluent.

4. The method of treating arterial hypertension in a patient in need thereof which comprises administering to such patient an amount effective therefore of a compound or salt thereof according to claim 1.

* * * * *